(12) United States Patent
Okumura et al.

(10) Patent No.: US 7,383,732 B2
(45) Date of Patent: Jun. 10, 2008

(54) DEVICE FOR INSPECTING MICRO STRUCTURE, METHOD FOR INSPECTING MICRO STRUCTURE AND PROGRAM FOR INSPECTING MICRO STRUCTURE

(75) Inventors: Katsuya Okumura, Tokyo (JP);
Toshiyuki Matsumoto, Amagasaki (JP);
Naoki Ikeuchi, Amagasaki (JP);
Masami Yakabe, Amagasaki (JP)

(73) Assignees: Octec Inc., Tokyo (JP); Tokyo Electron Limited, Tokyo (JP)

( * ) Notice: Subject to any disclaimer, the term of this patent is extended or adjusted under 35 U.S.C. 154(b) by 30 days.

(21) Appl. No.: 11/149,176

(22) Filed: Jun. 10, 2005

(65) Prior Publication Data

US 2005/0279170 A1    Dec. 22, 2005

(30) Foreign Application Priority Data

| Jun. 11, 2004 | (JP) | 2004-174423 |
| Mar. 9, 2005 | (JP) | 2005-064876 |
| May 31, 2005 | (JP) | 2005-160701 |

(51) Int. Cl.
*G01N 29/00* (2006.01)
*H01L 41/00* (2006.01)

(52) U.S. Cl. ............... 73/602; 73/584; 73/662; 310/334

(58) Field of Classification Search ........... 73/602, 73/584, 662, 649, 650, 651, 658, 663, 655; 310/334, 336, 338, 357, 358, 321
See application file for complete search history.

(56) References Cited

U.S. PATENT DOCUMENTS

| 4,816,125 A | 3/1989 | Muller et al. |
| 4,950,915 A | 8/1990 | Spies et al. |
| 5,269,185 A * | 12/1993 | Froidevaux ............ 73/430 |
| 5,747,692 A * | 5/1998 | Jacobsen et al. ......... 73/514.25 |

(Continued)

FOREIGN PATENT DOCUMENTS

EP    1 085 784 A2    3/2001

(Continued)

OTHER PUBLICATIONS

"Technology Research Report (Technology Tendency Compilation) No. 3", The Manufacturing Industry Bureau Industrial Machinery Section of The Ministry of Economy, Trade and Industry, Technology Environment Bureau Technology Research Division, pp. 1-16, (Mar. 28, 2003).

(Continued)

*Primary Examiner*—Hezron Williams
*Assistant Examiner*—Jacques M. Saint-Surin
(74) *Attorney, Agent, or Firm*—Finnegan, Henderson, Farabow, Garrett & Dunner LLP

(57) ABSTRACT

Test sound wave is outputted from a speaker. A movable part of a three-axis acceleration sensor, which is a micro structure of a chip to be tested TP, moves due to the arrival of the test sound wave which is compression wave outputted from the speaker, that is, due to air vibrations. A change in the resistance value that changes in accordance with this movement is measured on the basis of an output voltage that is provided via a probe needles. A control part determines the property of the three-axis acceleration sensor on the basis of the measured property values, that is, measured data.

30 Claims, 29 Drawing Sheets

U.S. PATENT DOCUMENTS

| | | | |
|---|---|---|---|
| 5,952,572 A * | 9/1999 | Yamashita et al. | 73/504.04 |
| 6,295,870 B1 * | 10/2001 | Hulsing, II | 73/514.37 |
| 6,507,187 B1 * | 1/2003 | Olivas et al. | 324/207.21 |
| 6,595,058 B2 * | 7/2003 | Lai et al. | 73/584 |
| 6,993,982 B2 * | 2/2006 | Karasawa et al. | 73/862.629 |
| 2002/0189357 A1 | 12/2002 | Lai et al. | |
| 2004/0007942 A1 | 1/2004 | Nishida et al. | |
| 2004/0066516 A1 | 4/2004 | Deacon et al. | |
| 2005/0023434 A1 | 2/2005 | Yacoubian | |
| 2007/0069746 A1 * | 3/2007 | Yakabe et al. | 324/754 |

FOREIGN PATENT DOCUMENTS

| | | |
|---|---|---|
| JP | 63-241459 | 10/1988 |
| JP | 01-502581 | 7/1989 |
| JP | 02-067956 | 3/1990 |
| JP | 05-034371 | 2/1993 |
| JP | 05-203485 | 8/1993 |
| JP | 06-313785 | 11/1994 |
| JP | 09-0333567 | 2/1997 |
| JP | 10-078454 | 3/1998 |
| JP | 11-002643 | 1/1999 |

OTHER PUBLICATIONS

Taniguchi, et al., "Micromachined 5-axis Motion Sensor with Electrostatic Drive and Capacitive Detection", Technical Digest of the 18th Sensor Symposium, pp. 377-380, (2001).

Partial European Search Report, Appl. No. EP 06006889.7-1528 Jul. 27, 2007.

Yacoubian et al., "EO Polymer-Based Integrated-Optical Acoustic Spectrum Analyzer", *IEEE Journal of Selected Topics in Quantum Electronics*, vol. 6, No. 5, pp. 810-816, (Sep./Oct. 2000).

European Search Report, Application No.: 05012547.5-1240, May 4, 2007.

Notice of Grounds of Rejection, Nov. 8, 2005, JP Patent Application No. 2005-160701.

Final Decision for Rejection, Sep. 5, 2006, JP Patent Application No. 2005-160701.

* cited by examiner

ACCELERATION ALONG X (Y) AXIS

ACCELERATION ALONG Z AXIS

OUTPUT ALONG X (Y) AXIS $$V_{xout} = \left( \frac{R_{x3}}{R_{x2}+R_{x3}} - \frac{R_{x4}}{R_{x1}+R_{x4}} \right) \cdot V_{dd}$$

OUTPUT ALONG Z AXIS $$V_{zout} = \left( \frac{R_{z3}}{R_{z1}+R_{z3}} - \frac{R_{z4}}{R_{z2}+R_{z4}} \right) \cdot V_{dd}$$

A: RESONANT FREQUENCY REGION
B: NON-RESONANT FREQUENCY REGION

TURNED OFF

CONTROL SIGNAL

TURNED ON

EDb

ED#

ED#a

DEVICE FOR INSPECTING MICRO STRUCTURE, METHOD FOR INSPECTING MICRO STRUCTURE AND PROGRAM FOR INSPECTING MICRO STRUCTURE

BACKGROUND OF THE INVENTION

1. Field of the Invention

The present invention relates to a device, a method and a program for inspecting micro structure, such as MEMS (Micro Electro Mechanical Systems).

2. Description of the Background Art

In recent years, MEMS which are devices where various functions, such as mechanical, electronic, optical and chemical functions, are integrated, particularly using a semiconductor microscopic processing or the like, have drawn attention. In accordance with MEMS technologies that have been put into practice so far, MEMS devices have been mounted as various types of sensors for, for example, automobiles and medical purposes, on micro sensors such as acceleration sensors, pressure sensors, air flow sensors, and the like. In addition, such MEMS technologies have been adopted in an inkjet printer head, and thereby, an increase in the number of nozzles for spewing an ink and precise spewing of an ink have become possible, making it possible to achieve an increase in the quality of pictures and an increase in the speed of printing. Furthermore, a micro mirror array or the like that is used in a reflection type projector is also known as a general MEMS device.

In addition, a variety of sensors and actuators will be developed by utilizing MEMS technologies in the future, and thereby, it is expected that application to optical communications and mobile apparatuses, application to peripheral apparatuses of computers, and application to biotechnological analysis and power sources for portable apparatuses will broaden. A variety of MEMS technologies are introduced in Technology Research Report Number 3 (issued by the Manufacturing Industry Bureau Industrial Machinery Section of the Ministry of Economy, Trade and Industry, Technology Environment Bureau Technology Research Division, on Mar. 28, 2003) under the agenda of state of the art and problems concerning MEMS.

Meanwhile, a system for appropriately inspecting MEMS devices are becoming more and more important, because of the micro structure thereof, as MEMS devices develop. Though the property of devices have been evaluated by rotating the devices after packaging or by using means such as vibration according to the prior art, it will become possible to increase the yield and reduce the manufacturing cost by detecting defects as a result of appropriate inspection carried out in the initial step, where the devices are in the state of wafers, after the application of a microscopic processing.

In Japanese Laid-Open Patent Publication No. 05-034371, an inspection system for detecting the resistance value of an acceleration sensor that changes by blowing air against the acceleration sensor formed on a wafer, and thereby, for determining the property of the acceleration sensor, has been proposed as an example.

In general, a structure having a microscopic moveable part, such as an acceleration sensor, is a device of which the response property change in accordance with a microscopic movement. Accordingly, it is necessary to carry out inspection with high precision, in order to evaluate these property. Though the property of an acceleration sensor must be evaluated by carrying out microscopic adjustment, even in the case where a device is changed by blowing air to the device as shown in the above-described gazette, it is extremely difficult to carry out inspection with high precision by controlling the amount of gas flow, and at the same time uniformly blowing a gas against the device, and a complex, expensive tester must be provided, even when such inspection is implemented.

SUMMARY OF THE INVENTION

The present invention is achieved in order to solve the above-described problem, and an object thereof is to provide a method, a unit and a program for inspecting a structure having a microscopic moveable part with high precision and in a simple system.

A device for inspecting a micro structure according to the present invention is a device for inspecting a micro structure having a moveable part formed on a substrate which evaluates the property of at least one micro structure, and which is provided with a sound wave generator for outputting a test sound wave to a micro structure at the time of testing. The movement of the movable part of a micro structure in response to sound wave that has been outputted by the sound wave generator is detected, and the property of the micro structure is evaluated on the basis of the detection result.

Preferably, a number of micro structure, each of which is the same as the micro structure, are arranged in array form on the substrate.

Preferably, the unit detects the movement of the movable part of a micro structure in response to test sound wave that has been outputted by the sound wave generator, and is further provided with an evaluator for evaluating the property of the micro structure on the basis of the detection result.

In particular, the evaluator includes a change amount detector for detecting the amount of change that changes on the basis of the movement of the moveable part of a micro structure, and a determinator for evaluating the property of the micro structure on the basis of the comparison between the amount of change that has been detected by the change amount detector and the amount of change that becomes a predetermined threshold.

In particular, the change amount detector detects the amount of change in the impedance that changes on the basis of the movement of the moveable part of a micro structure, and the determinator evaluates the property of the micro structure by comparing the amount of change in the impedance that has been detected by the change amount detector with the amount of change in the impedance that becomes a predetermined threshold.

In particular, the determinator evaluates the property of a micro structure by comparing the frequency that corresponds to the maximum amount of change that has been detected by the change amount detector with a desired frequency that corresponds to the amount of change that becomes a predetermined threshold.

In particular, the evaluator includes a positional displacement detector for detecting the amount of displacement of the moveable part of a micro structure that displaces on the basis of the movement of the moveable part of the micro structure, and a determinator for evaluating the property of the micro structure on the basis of a comparison between the amount of displacement that has been detected by the positional displacement detector the amount of displacement that becomes a predetermined threshold.

In particular, the positional displacement detector detects an electrostatic capacitance that changes on the basis of the movement of the moveable part of a micro structure, and the determinator evaluates the property of the micro structure by comparing the electrostatic capacitance that has been detected by the positional displacement detector with the electrostatic capacitance that becomes a predetermined threshold.

In particular, the positional displacement detector detects the amount of displacement on the basis of the movement of the movable part of a micro structure using a laser.

In particular, the determinator evaluates the property of a micro structure by comparing the frequency that corresponds to the maximum amount of displacement that has been detected by the positional displacement detector with a desired frequency that corresponds to the amount of displacement that becomes a predetermined threshold.

Preferably, the sound wave generator includes a sound wave outputting part for outputting test sound wave having a sound pressure in accordance with an input from the outside, a detector for detecting test sound wave that reaches the proximity of a micro structure, and a sound wave corrector for correcting test sound wave that has been outputted from the sound wave outputting part by comparing the sound pressure level of the test sound wave that has been detected by the detector with the sound pressure level of predetermined test sound wave that becomes a reference.

In particular, the sound wave generator further includes a noise remover for removing a noise sound wave that reaches a micro structure from the outside.

In particular, the noise remover outputs an anti-noise sound wave which is in phases that is opposite to those of noise sound wave and has the same frequency and sound pressure as the noise sound wave so as to cancel the noise sound wave, on the basis of the noise sound wave that has been detected by the detector before testing.

In particular, the anti-noise sound wave is outputted from the sound wave outputting part together with the test sound wave at the time of testing.

In particular, the evaluator receives the detection result of test sound wave that has been detected by the detector of the sound wave generator, and outputs the determination result by means of the determinator.

Preferably, a micro structure corresponds to at least one of an acceleration sensor and an angular sensor.

In particular, the acceleration sensor and the angular rate sensor respectively correspond to a multi-axial acceleration sensor and a multi-anal angular rate sensor.

A device for inspecting a micro structure according to the present invention is a device for inspecting a micro structure which evaluates the property of at least one micro structure having a moveable part formed on a substrate, and which is provided with a sound wave generator for outputting test sound wave to a micro structure at the time of testing and an evaluator for evaluating the property of a micro structure on the basis of the detection result when the unit detects the movement of the moveable part of a micro structure in response to the test sound wave that has been outputted from the sound wave generator, wherein the evaluator includes: an electrostatic capacitance detection electrode that is installed so as to face the moveable part of a micro structure; a capacitance detector for detecting electrostatic capacitance between the electrostatic capacitance detection electrode and the moveable part of the micro structure, which changes on the basis of the movement of the moveable part of the micro structure; and a determinator for evaluating the property of the micro structure on the basis of a comparison between the electrostatic capacitance that has changed and been detected by the capacitance detector, and the electrostatic capacitance that becomes a predetermined threshold.

In particular, the evaluator detects at least two movements of the movable part of the micro structure simultaneously and uses a resultant detection to evaluate at least two properties of the micro structure simultaneously.

In particular, the evaluator detects movements in at least two directions of the movable part of the micro structure simultaneously and uses a resultant detection to evaluate properties in at least two directions of the micro structure simultaneously.

In particular, if the micro structure has at least two movable parts and/or the substrate has at least two micro structure thereon, preferably the evaluator detects the at least two movable parts' respective movements simultaneously and uses a resultant detection to evaluate simultaneously properties of the at least two movable parts, respectively, of the micro structure or the at least two micro structure.

Preferably, if the at least two movable parts have different property, respectively, in movability, the evaluator detects the at least two movable parts' respective movements simultaneously and uses a resultant detection to simultaneously evaluate properties of the at least two movable parts, respectively, having different properties, respectively, in movability.

Preferably the sound wave generator outputs as the lest sound wave a composite wave including at least two sound waves different in frequency.

Preferably, the sound wave generator outputs white noise as test sound wave.

In particular, the sound wave generator outputs as the test sound wave a white noise in a prescribed frequency range.

A method for inspecting a micro structure according to the present invention is provided with the step of supplying a test sound wave Lo at least one micro structure having a moveable part formed on a substrate, the step of detecting the movement of the moveable part of the micro structure in response to the test sound wave, and the step of evaluating the property of the micro structure on the basis of the detection result.

In particular, the step of detecting detects simultaneously at least two movements of the movable part of the micro structure; and the step of evaluating evaluates simultaneously at least two properties of the micro structure.

Preferably the step of supplying supplies a white noise as the test sound wave.

A program for inspecting a micro structure according to the present invention allows a computer to implement a method for inspecting a micro structure which includes the step of supplying a test sound wave to at least one micro structure having a moveable part formed on a substrate, the step of detecting the movement of the moveable part of the micro structure in response to the test sound wave, and the step of evaluating the property of the micro structure on the basis of the detection result.

In particular, the step of detecting detects simultaneously at least two movements of the movable part of the micro structure, and the step of evaluating evaluates simultaneously at least two properties of the micro structure.

Preferably the step of supplying supplies white noise as the test sound wave.

In accordance with a method, a unit and a program for inspecting a micro structure according to the present invention, test sound wave is supplied to a micro structure and the movement of the moveable part of the micro structure is detected, and thereby, the property thereof are evaluated. The moveable part of the micro structure is moved by means of air vibrations using sound wave, which is compression wave, so that the property thereof can be evaluated, and therefore, the micro structure can be inspected with a simple system.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
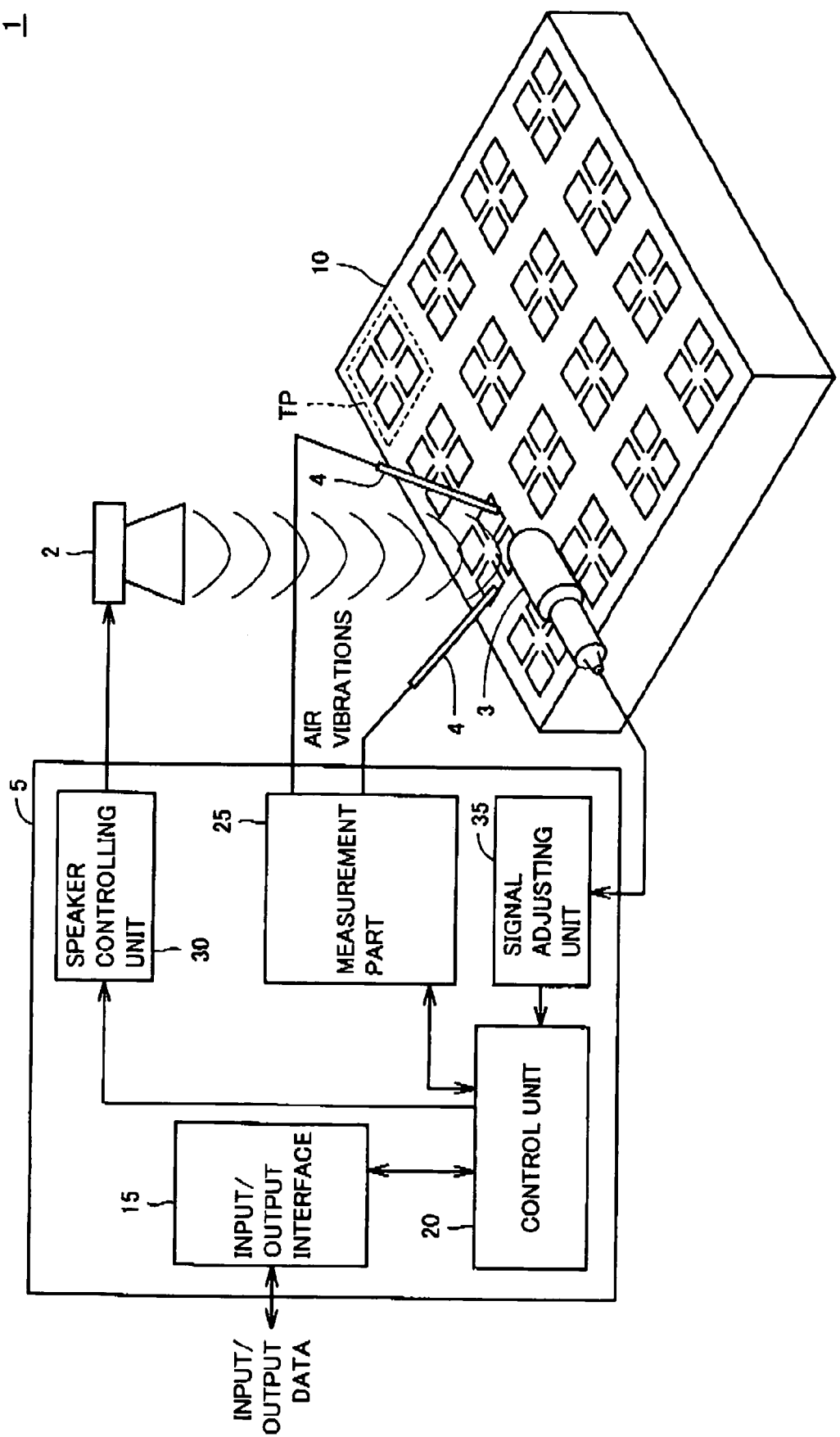
FIG. 1 is a schematic configuration diagram showing a system for inspecting a micro structure according to a first embodiment of the present invention.

In the following, the embodiments of this invention are described in detail, with reference to the drawings. Here, the same symbols are attached to parts that are the same as or corresponding to those in the drawings, and the descriptions thereof are not repeated.

First Embodiment

With reference to FIG. 1, a system 1 for inspecting a micro structure according to a first embodiment of the present invention is provided with a tester (inspection device) 5 and a substrate 10 where a number of chips TP of micro structure having microscopic moveable parts are formed.

In the present embodiment, a three-axis acceleration sensor which has multiple axes is cited and described as an example of a micro structure that is to be tested.

Tester 5 is provided with a speaker 2 for outputting sound wave which is compression wave, an input/output interface 15 for transferring input/output data between the outside and the inside of the tester, a control unit 20 for controlling the entirety of tester 5, probe needles 4 which are used to make contact with the test object, a speaker controlling unit 30 for controlling speaker 2 in response to an instruction from control unit 20, a microphone 3 for detecting sound from the outside, and a signal adjusting unit 35 for converting the sound wave that has been detected by microphone 3 into a voltage signal, and furthermore, for amplifying the voltage signal which is then outputted to control unit 20. Here, it is possible to place microphone 3 in the vicinity of the test object.

Figure 2:
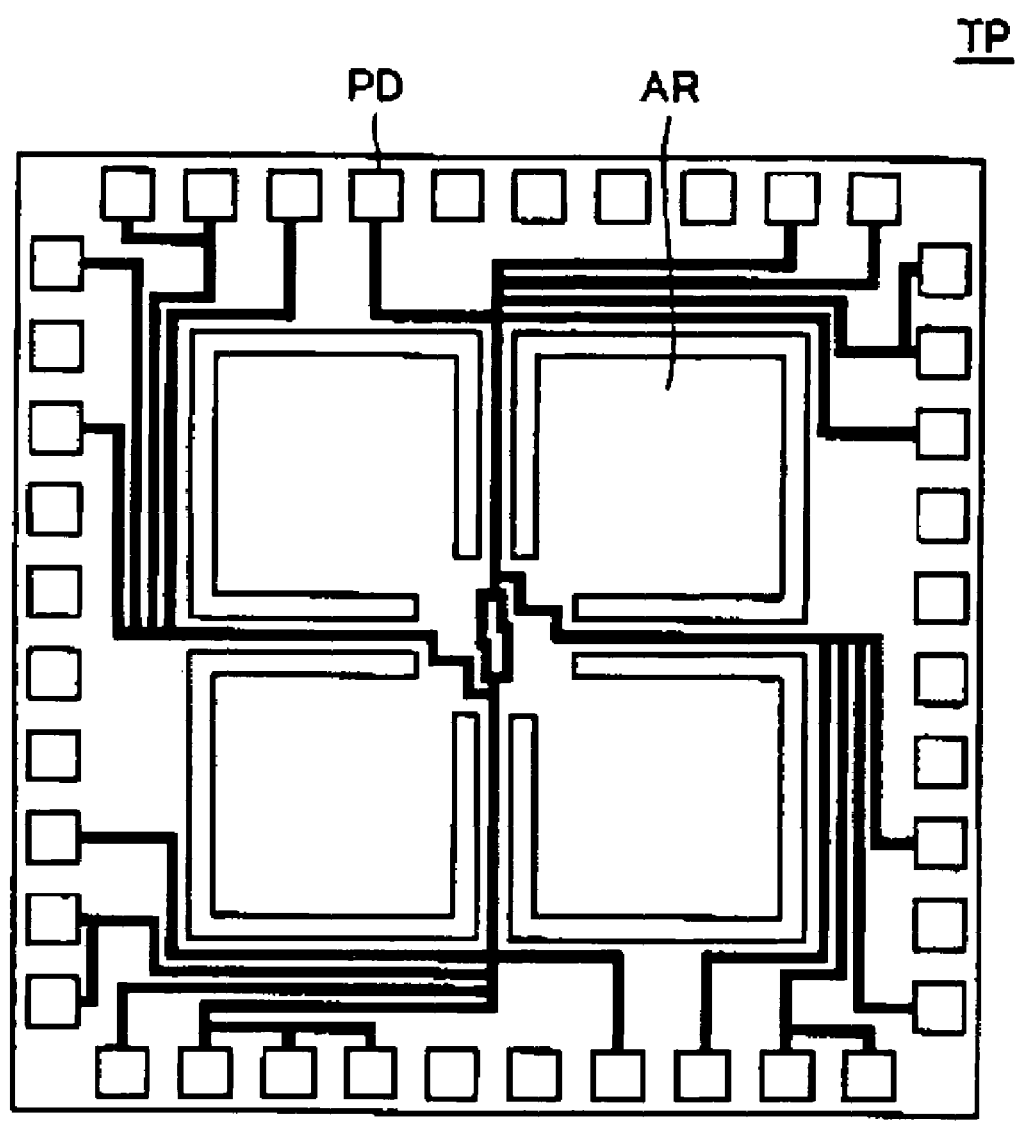
FIG. 2 is a diagram showing a device of a three-axis acceleration sensor as viewed from above.

First, the three-axis acceleration sensor of a micro structure which is the test object is described, before describing the inspection method according to the present embodiment, As shown in FIG. 2, a number of pads PD are placed around the periphery of a chip TP that is formed on a substrate 10 as viewed from the top of a three-axis acceleration sensor device. In addition, metal wires for transmitting an electrical signal to a pad or for transmitting an electrical signal from a pad are provided. Furthermore, four proof masses AR that form a four-leafed clover shape are placed in the center portion.

Figure 3:
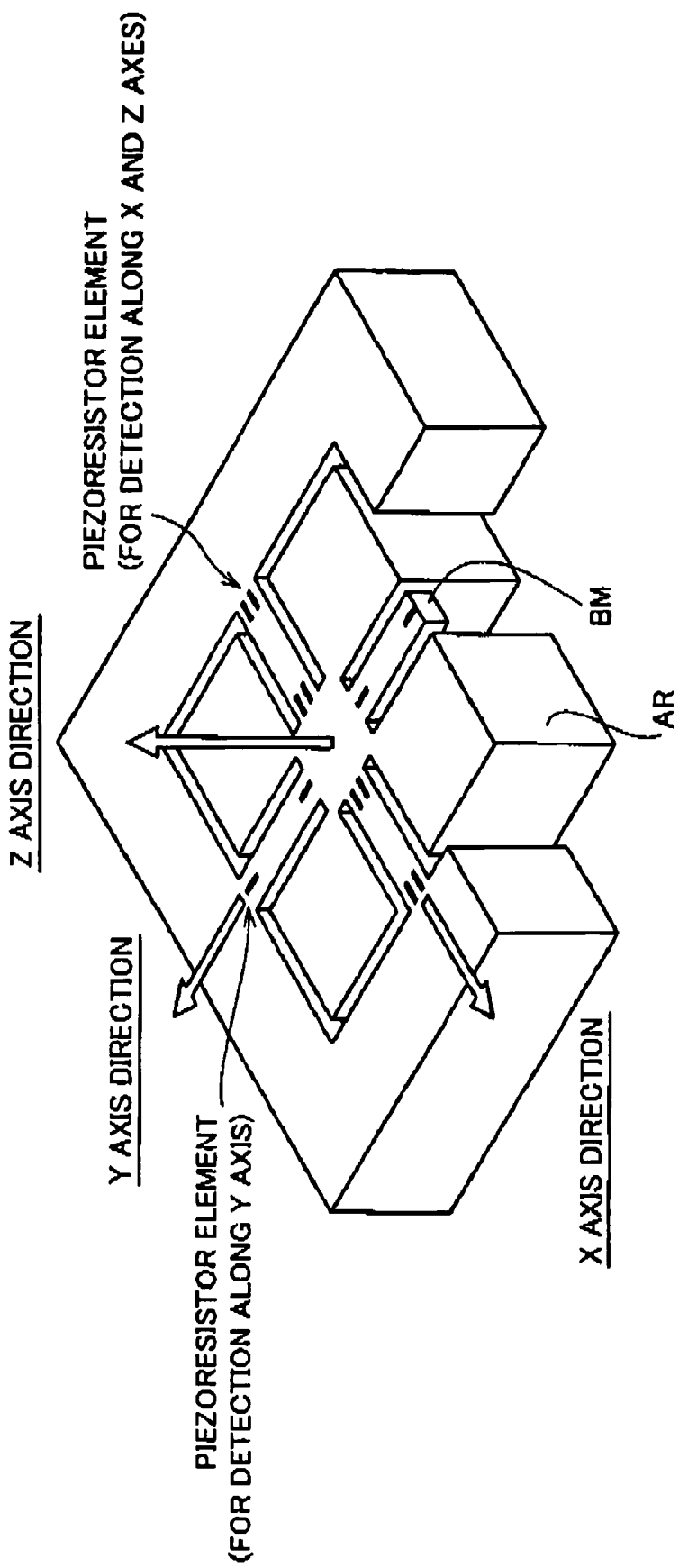
FIG. 3 is a schematic diagram showing the three-axis acceleration sensor.

With reference to FIG. 3, this three-axis acceleration sensor is of a piezoresistive element type, and a piezoresistive element which is a detection element is provided as resistance of diffused region. This piezoresistive element type acceleration sensor can be made using an inexpensive IC process, and the sensitivity is not lowered, even in the case where the resistor element that is a detection element is formed so as to be small, and therefore, this acceleration sensor is advantageous for miniaturization and reduction in cost.

Proof masses AR at the center have structures that are supported by four beams BM in a concrete configuration. Beams BM are formed so as to be perpendicular to each other in the two axial directions X and Y, where four piezoresistive elements are provided for each axis. Four piezoresistive elements for detection in the direction of the Z axis are provided on the side of the piezoresistive elements for detection in the direction of the X axis. The form of the upper surface of proof masses AR is in four-leafed clover form, and proof masses AR are linked to beams BM in the center portion. It becomes possible to implement a highly sensitive acceleration sensor which is compact, even though the size of proof masses AR is increased and at the same time the length of the beams is increased, by adopting this four-leafed clover type structure.

The sensing mechanism of the three-axis acceleration sensor of this piezoresistive element type provides a mechanism where beams BM are deformed when the proof masses receive acceleration (force of inertia) and the acceleration is detected due to a change in the resistance values of the piezoresistive elements which have been formed on the surface of the beams. In addition, this output of the sensor is set to be taken out in the configuration as the output of the below described Wheatstone's bridge, where three axes are independently associated.

Figure 4:
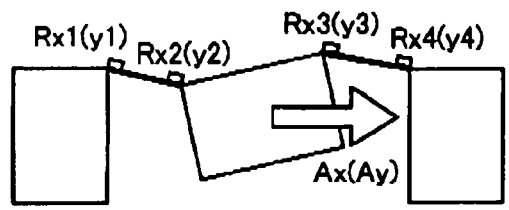
FIG. 4 is a conceptual diagram for illustrating proof masses and deformation of beams in the case where an acceleration is applied in the direction of each axis.
Figure 4:
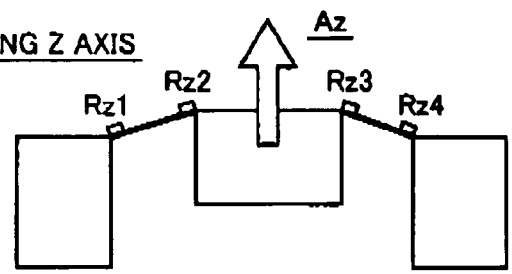

With reference to FIG. 4, deformation of the proof masses and the beams in the case where acceleration is received in the direction of each axis is described.

As shown in FIG. 4, a piezoresistive element has property where the resistance value thereof changes due to a warp that has been caused (piezoresistive element effect), in a manner where the resistance value increases in the case of a warp caused by stretching and the resistance value decreases in the case of a warp caused by compression, In the present embodiment, piezoresistive elements for detection in the direction of the X axis Rx1 to Rx4, piezoresistive elements for detection in the direction of the Y axis Ry1 to Ry4, and piezoresistive elements for detection in the direction of the Z axis Rz1 to Rz4 are shown as examples.

Figure 5A:
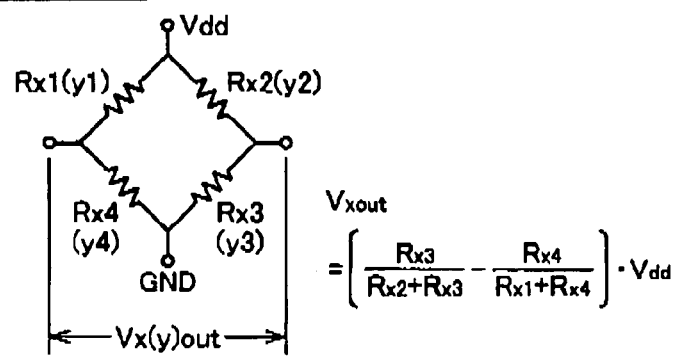
FIGS. 5A and 5B are circuit configuration diagrams showing Wheatstone's bridges provided for each axis.

FIG. 5A is a circuit configuration diagram of a Wheatstone's bridge along the X (Y) axis. The output voltages of the X axis and the Y axis are assumed to be Vxout and Vyout, respectively.

FIG. 51B is a circuit configuration diagram of a Wheatstone's bridge along the Z axis. The output voltage of the Z axis is assumed to be Vzout.

As described above, the resistance values of the four piezoresistive elements along each axis change due to a warp that has been caused, and on the basis of this change, the circuit that is formed as a Wheatstone's bridge by each piezoresistive element along, for example, the X axis and the Y axis, detects the acceleration component along each axis of the output as an independent, separate output voltage. Here, the above-described metal wires and the like, as shown in FIG. 2, are linked so that a circuit as described above is formed, and an output voltage for each axis is detected from a predetermined pad in the configuration.

In addition, this three-axis acceleration sensor can detect the DC component of acceleration, and therefore, it is possible to use this three-axis acceleration sensor as an inclination angle sensor for detecting acceleration in the gravity, that is, as an angular rate sensor.

Figure 6A:
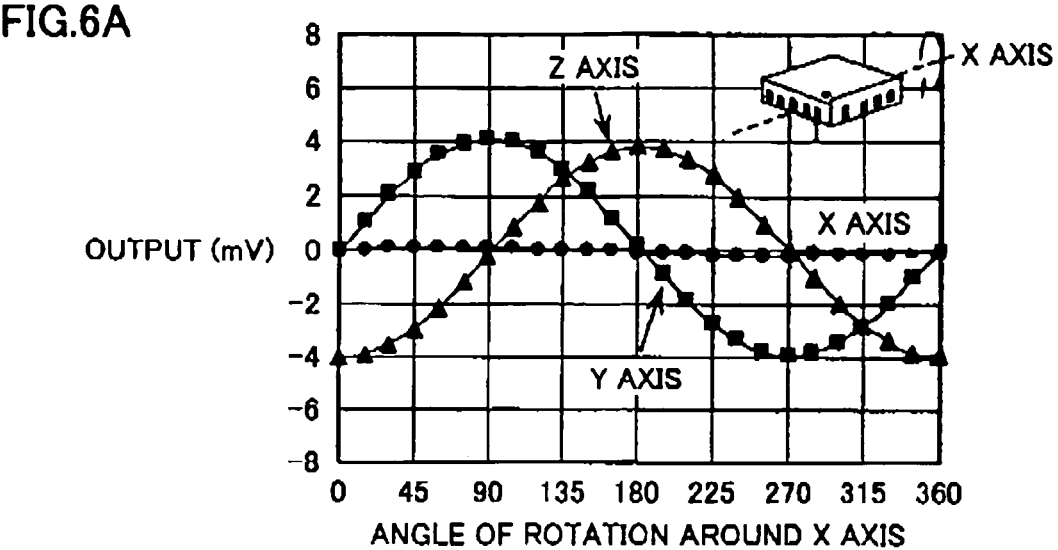
FIGS. 6A to 6C are graphs for describing an output response relative to an inclination angle of a three-axis acceleration sensor.
Figure 6B:
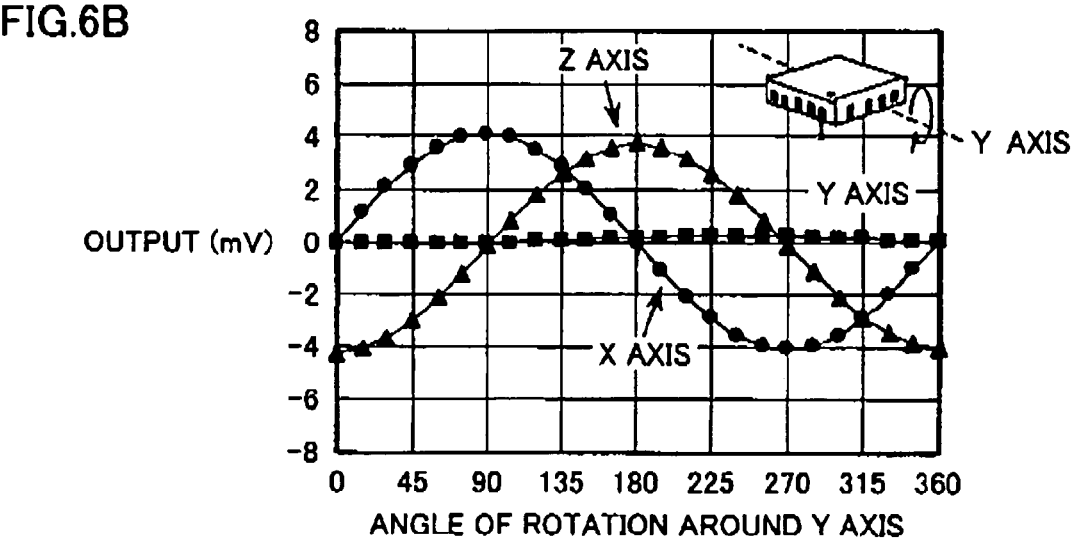
Figure 6C:
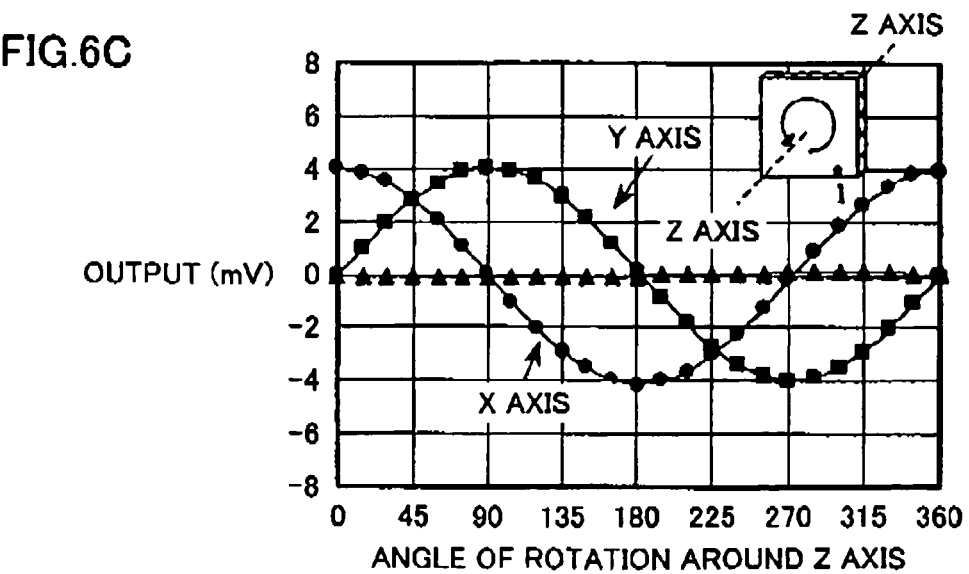

With reference to FIGS. 6A to 6C, the output response to the inclination angle of a three-axis acceleration sensor is described.

As shown in FIGS. 6A to 6C, a sensor is rotated around the X, Y and Z axes so that the respective bridge outputs of the X Y and Z axes are respectively measured by a digital voltage meter. A low voltage power supply of +5 V is utilized as the power supply for the sensor. Here, values from which the offsets of the respective axial outputs have been arithmetically decreased are plotted as the respective measurement points shown in FIGS. 6A to 6C.

Figure 7:
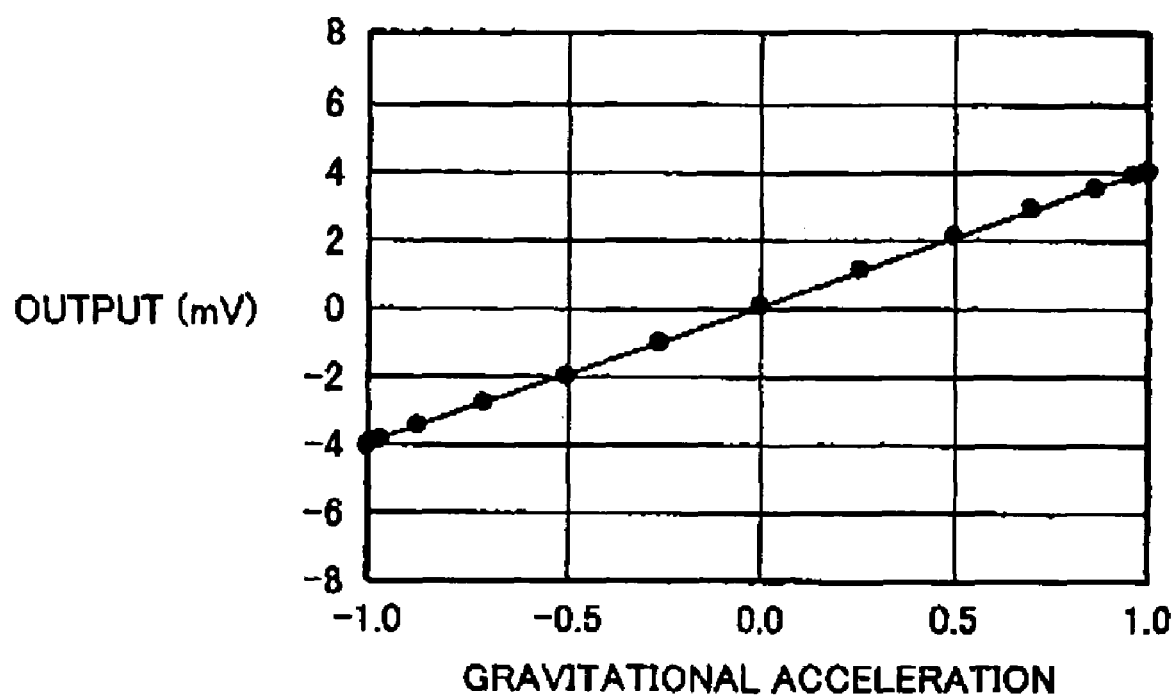
FIG. 7 is a graph for illustrating the relationship between the gravity acceleration (input) and output of sensor.

With reference to FIG. 7, the relationship between gravity acceleration (input) and sense outputs is described.

The input/output relationship shown in FIG. 7 is gained by calculating the gravity acceleration components which respectively relate to the X, Y and Z axes form the cosines of the inclination angles of FIGS. 6A to 6C so as to find the relationship between the gravity acceleration (input) and the output of the sensor, and by evaluating the linearity of this input/output. That is, the relationship between the acceleration and the output voltage is approximately linear.

When the three-axis acceleration sensor('s proof mass AR) is vibrated for example along the Z axis and the three-axis acceleration sensor rotates around the X or Y axis (or other than the Z axis), Coriolis force acts on proof mass AR As Coriolis force's direction and magnitude can be detected, the three-axis acceleration sensor can be used as an angular rate sensor. A method employing a three-axis acceleration sensor to measure angular speed is more specifically described for example by Nobumitsu Taniguchi, et al. "Micromachined 5-axis Motion Sensor with Electrostatic Drive and Capacitive Detection", Technical Digest of the 18th Sensor Symposium, 2001, pp. 377-380.

Figure 8A:
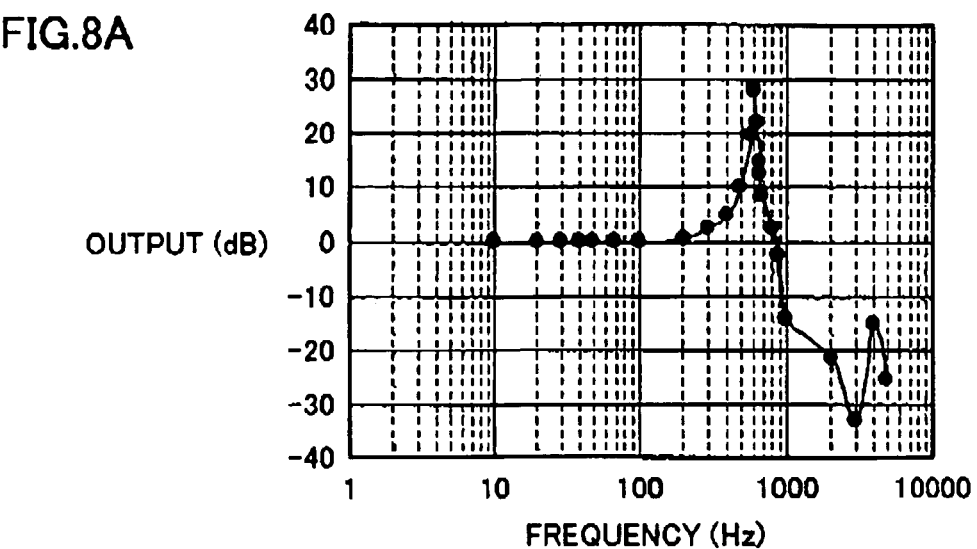
FIGS. 8A to 8C are graphs for illustrating frequency properties of a three-axis acceleration sensor.
Figure 8B:
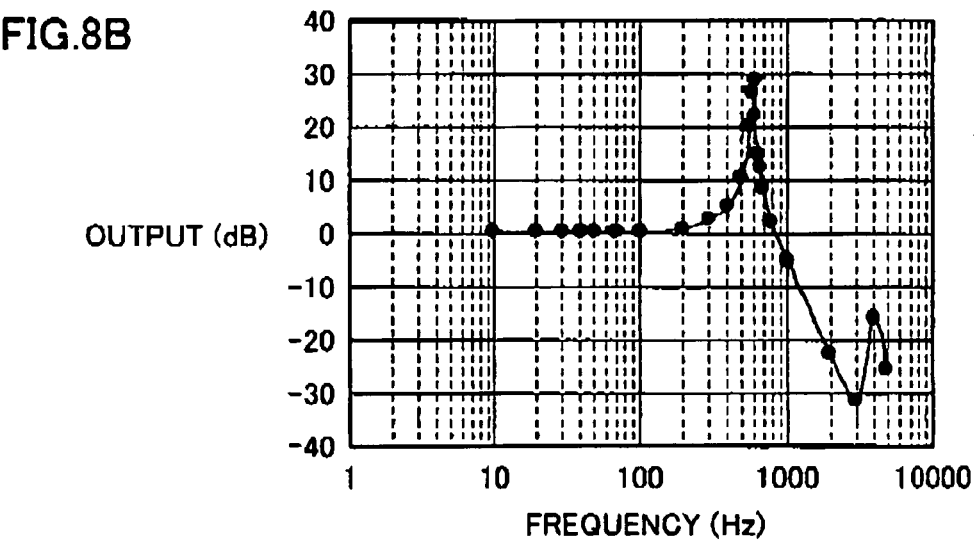
Figure 8C:
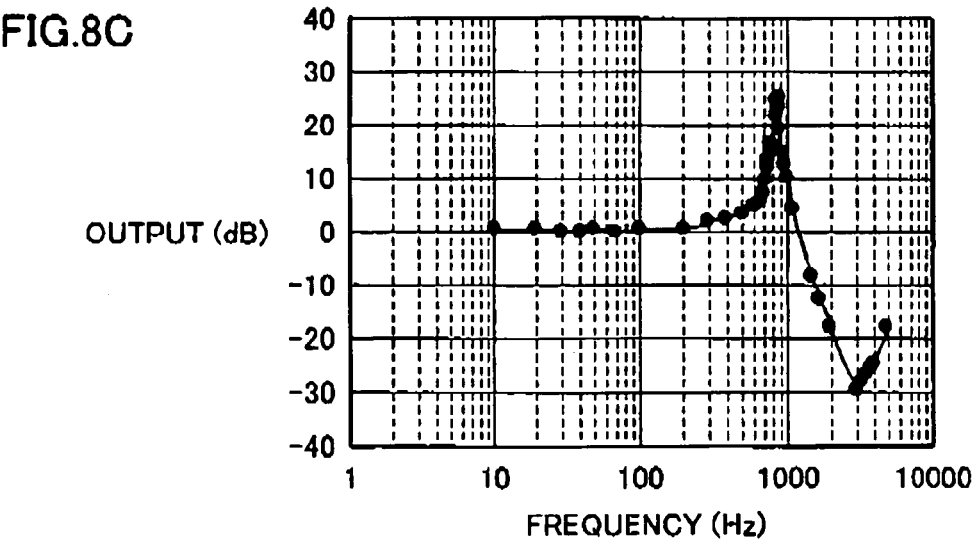

With reference to FIGS. 8A to 8C, the frequency properties of the three-axis acceleration sensor are described.

Figure 5B:
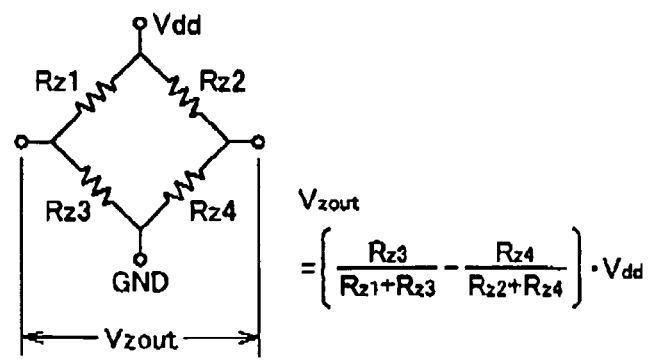

As shown in FIGS. 5A to 5C, the frequency properties of the outputs of sensors along the X, Y and Z axes, respectively, are indicated as flat frequency properties up to the vicinity of 200 Hz along all of the there axes, in an example where there are resonations at 602 Hz along the X axis, at 600 Hz along the Y axis and at 883 Hz along the Z axis.

With reference to FIG. 1 again, a method for inspecting a micro structure according to the embodiment of the present invention provides a system for outputting sound wave which is compression wave to a three-axis acceleration sensor that is a micro structure, and thereby, detecting the movement of the moveable part of the micro structure on the basis of these sound wave, so as to evaluate the property thereof. With reference to the flowchart of FIG. 9, a method for inspecting a micro structure according to the first embodiment of the present invention is described.

Figure 9:
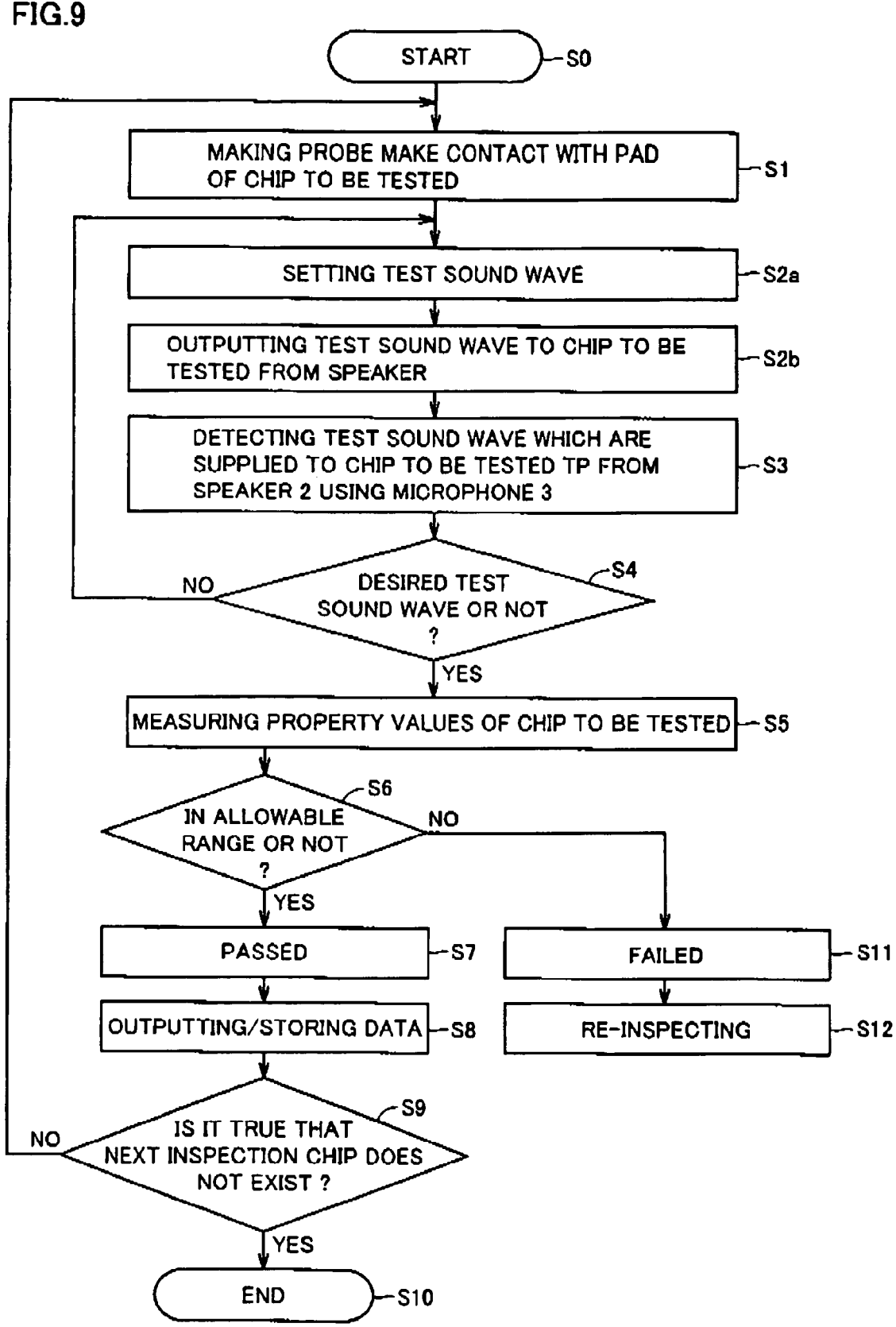
FIG. 9 is a flowchart for illustrating a method for inspecting a micro structure according to the first embodiment of the present invention.

With reference to FIG. 9, first, inspection (testing) of a micro structure is started (step S0). Next, probe needles 4 are made to make contact with pads PD of chip to be tested TP (step S1). Specifically speaking, probe needles 4 are made to make contact with predetermined pads PD in order to detect the output voltage of the Wheatstone's bridge circuit described in FIG. 5. Here, though FIG. 1 shows a configuration where a pair of probe needles 4 is used, it is possible to provide a configuration where a number of pairs of probe needles are used. Employing a plurality of pairs of probe needles allows detecting, in parallel, signals output from a plurality of outputs of a single chip TP and/or a plurality of chips TPs.

Next, test sound wave that is outputted from speaker 2 are set (step S2a). Specifically speaking, control unit 20 receives an input of input data from the outside via input/output interface 15. Then, control unit 20 controls speaker controlling unit 30 and instructs speaker controlling unit 30 so that test sound wave having a desired frequency and a desired sound pressure are outputted from speaker 2 on the basis of the input data. Next, test sound wave is outputted from speaker 2 to chip to be tested TP (step S2b).

Next, microphone 3 is used to detect test sound wave which is supplied to chip to be tested TP from speaker 2 (step S3). The test sound wave that has been detected by microphone 3 are converted to a voltage signal which is then amplified in signal adjusting unit 35, and the resulting signal is outputted to control unit 20.

Next, control unit 20 analyzes and determines the voltage signal that is inputted from signal adjusting unit 35, and determines whether or not desired test sound wave has reached the control unit (step S4).

In the case where control unit 20 determines desired test sound wave in step S4, the procedure goes to the next step S5, where the property value of the chip to be tested is measured. Specifically speaking, the property value is measured in measurement part 25 on the basis of an electrical signal that is transmitted via probe needles 4 (step S5).

Specifically speaking, the moveable part of a micro structure of the chip to be tested moves due to the arrival of test sound wave which is compression wave outputted form speaker 2, that is, air vibrations. A change in the resistance value of the three-axis acceleration sensor which is the micro structure that changes on the basis of this movement is measured on the basis of the output voltage that is supplied via probe needles 4.

Meanwhile, in the case where the signal is determined not to be desired test sound wave in step S4, the procedure returns to step S2a again, and the test sound wave is reset. At this time, control unit 20 instructs speaker controlling unit 30 to correct the test sound wave. Speaker controlling unit 30 microscopically adjusts the frequency and/or the sound pressure so as to gain desired test sound wave in response to the instruction from control unit 20, and thus, controls the system so that the desired test sound wave is outputted from speaker 2. Here, though a system where test sound wave is detected and corrected to desired test sound wave is described in the present embodiment, it is possible to provide a configuration where a part for correcting test sound wave and a system for correcting test sound wave are not particularly provided in the cases desired test sound wave reaches the micro structure of the chip to be tested in advance. Specifically speaking, processing up to steps S2a to S4 is implemented in advance before the start of testing, and a corrected control value for outputting desired test sound wave is stored in speaker controlling unit 30. Then, at the time of testing of the actual micro structure, speaker controlling unit 30 controls the input to speaker 2 with this recorded control value, and thereby, it becomes possible to omit the above-described processing in steps S3 and S4 at the time of testing.

Next, control unit 20 determines whether or not the measured property value, that is, measured data, is in an allowable range (step S6). In the case where it is determined to be in the allowable range in step S6, it is passed (step S7), and the outputting and storing of data are implemented (step S8). Then, the procedure goes to step S9. As an example of determination in the allowable range, in control unit 20, it is determined whether or not a desired output voltage is gained in response to the sound pressure of test sound wave which is outputted from speaker 2, or more concretely, whether or not the resistance value of the three-axis acceleration sensor changes in linear form in response to a change in the sound pressure of the test sound wave which is outputted from speaker, that is, whether or not the linear relationship described in FIG. 7 is gained, and thereby, whether or not the chip has appropriate property, can be determined. Here, data is stored in a storage unit, such as a memory, not shown, that is provided inside tester 5 on the basis of an instruction from control unit 20.

In the case where there is no chip to be inspected next in step S9, the inspection (testing) of a micro structure is completed (step S10).

Meanwhile, in the case where a chip to be inspected next exists in step S9, the procedure returns to the initial step S1, and the above-described inspection is again implemented.

Here, in the case where control unit 20 determines that the measured property value, that is, the measured data, is not in the allowable range in step S6, it is failed (step S11) and re-inspection is carried out (step S12). Specifically speaking, a chip that is determined to be outside of the allowable range can be removed through re-inspection. Alternatively, chips that are determined to be outside of the allowable range can be divided into a number of groups. That is, it is considered that many chips exist which are chips that cannot pass strict test conditions but do not cause any problems even if they are shipped after modification and correction. Accordingly, it is possible to select chips by grouping the chips through re-inspection and the like, and to ship some of the chips on the basis of the selection result.

Here, though in the present embodiment, a configuration is described as an example where a change in the resistance value of a piezoresistive element that is provided in a three-axis acceleration sensor is detected and determined by means of an output voltage in response to the movement of the three-axis acceleration sensor, it is also possible to provide a configuration where a change in the impedance value, such as that of a capacitor element or a reactance element, without being particularly limited to a resistor element, or a change in the voltage, the current, the frequency, the phase difference, the delay time and the position on the basis of a change in the impedance value is detected and determined.

Figure 10:
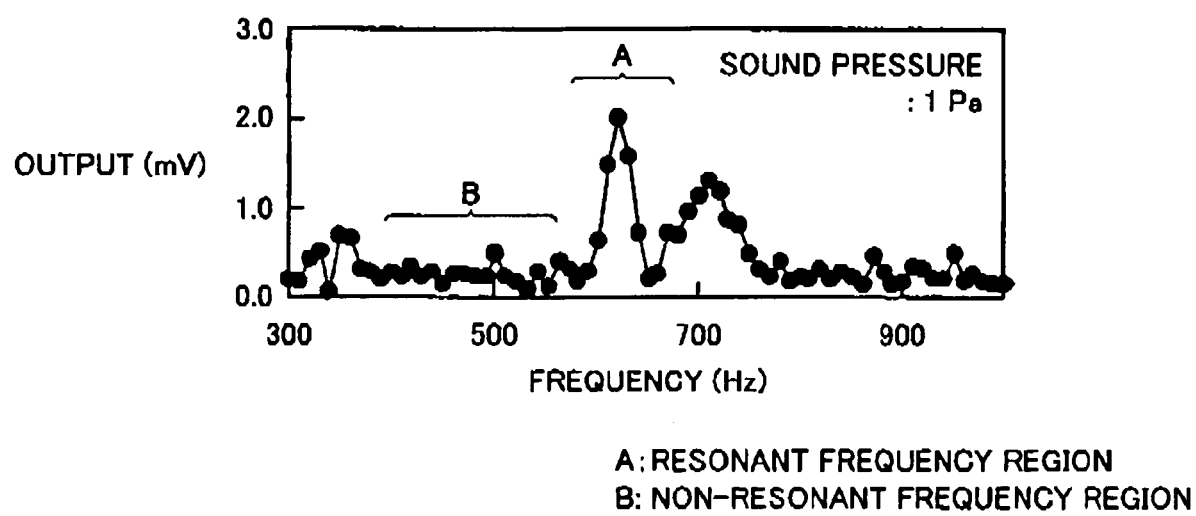
FIG. 10 is a graph for illustrating the frequency response of a three-axis acceleration sensor that responds to test sound wave that has been outputted from a speaker.

With reference to FIG. 10, the frequency response of a three-axis acceleration sensor that responds to test sound wave that has been outputted from speaker 2 is described.

FIG. 10 shows the output voltage that is outputted from a three-axis acceleration sensor in the case where test sound wave of 1 Pa (Pascal) is supplied as sound pressure, and the frequency thereof is changed. The vertical axis indicates the output voltage (mV) of the three-axis acceleration sensor, and the horizontal axis indicates the frequency (Hz) of the test sound wave.

Here, the output voltage that is gained in the direction of the X axis is particularly shown.

FIG. 10 shows two regions A and B. Specifically speaking, FIG. 10 shows resonant frequency region A, and non resonant frequency region B.

With reference to FIG. 10, the frequency where the output voltage is the maximum, that is, where the maximum output voltage that has changed as a result of resonation is gained corresponds to the resonant frequency. In FIG. 10, the frequency that corresponds to this output is approximately 600 Hz. That is, it almost coincides with the frequency property of the three-axis acceleration sensor along the X axis.

Accordingly, it is possible to specify the resonant frequency from the property of the output voltage that are gained when, for example, the frequency of test sound wave is changed while making the sound pressure constant, and it becomes possible to determine whether or not this specified resonant frequency is a desired resonant frequency after the comparison between this specified frequency and the desired resonant frequency. Though only the X axis is illustrated in the present embodiment, it is possible to gain the frequency properties along the X axis and the Z axis in the same manner, and therefore, the properties of the acceleration sensor along the three respective axes can be evaluated simultaneously.

In the case where, for example, resonation occurs in a frequency other than 600 Hz that is not the resonant frequency, an appropriate and desired frequency cannot be gained along this axis, and therefore, it is possible to determine that the system is defective. That is, it is difficult to conduct inspection from the appearance, particularly because this is a micro structure, while damage in the internal structure and a crack or the like that has occurred in the moveable part of the micro structure can be inspected in the above-described manner. Here, though a case where the resonant frequency is specified from the maximum output voltage is described, the moveable part has the maximum amount of displacement as a result of resonation, Accordingly, the frequency where the maximum amount of displacement is gained corresponds to the resonant frequency. As a result of this, the resonant frequency is specified from the maximum amount of displacement, and it is possible to determine whether or not a desired resonant frequency has been gained in the same manner as described above, so as to see if there are defects.

In addition, it is also possible to change the sound pressure of test sound wave using, for example, the frequency region of region B, that is, the non resonant frequency region, so as to perform detection and inspection of the sensitivity and the offset of a three-axis acceleration sensor from the output result.

Furthermore, though a system for inspecting one chip TP via probe needles 4 is described in the present embodiment, test sound wave spreads uniformly, and therefore, it is also possible to perform the same inspection on a number of chips in parallel, In addition, it is relatively easy to control the frequency and sound pressure of test sound wave, and therefore, the configuration of the unit can be made to be simple and easy, in comparison with the configuration of the unit for controlling the amount of flow of air.

As described above, the property of a micro structure can be inspected with high precision from the movement of the moveable part of the micro structure in the configuration of an inspection method and an inspection device according to the first embodiment, which is a simple system for controlling sound wave which is compression wave.

Here, it is possible to store a program in advance for allowing a computer to implement an inspection method according to the first embodiment that is described in the flowchart of FIG. 9 in a recording medium, such as an IFD, a CD-ROM or a hard disk. In such a case, a driver unit that reads the program that has been stored in a recording medium is provided in tester 5, and control unit 20 receives the program via the driver unit and stores the program in a memory within control unit 20, and thereby, it is possible to carry out the above-described inspection method. Furthermore, in the case where the system is connected to a network, it is possible for this program to be downloaded from a server so that control unit 20 can carry out the above-described inspection method. Here, it is also possible to store a program for allowing a computer to implement an inspection method according to the below described embodiments and modifications of these in a recording medium in the same manner, so that control unit 20 can carry out the inspection method in the same manner as described above.

Here, the inspection system described in Japanese Laid-Open Patent Publication No. 05-034371 has a configuration where the property of an acceleration sensor device having one axis are inspected by blowing air against the device, and the properties of a multi-axial acceleration sensor cannot be inspected without changing the direction (angle) from which air is blown against the device. However, it is possible, in the system of the present configuration, to inspect the properties of the respective axes simultaneously from the movement of the moveable body of a multi-axial acceleration sensor, due to air vibrations.

Modification of First Embodiment

According to a modification of the first embodiment of the present invention, a case is described where property of a micro structure are evaluated in a system that is different from the one described in the first embodiment.

Figure 11:
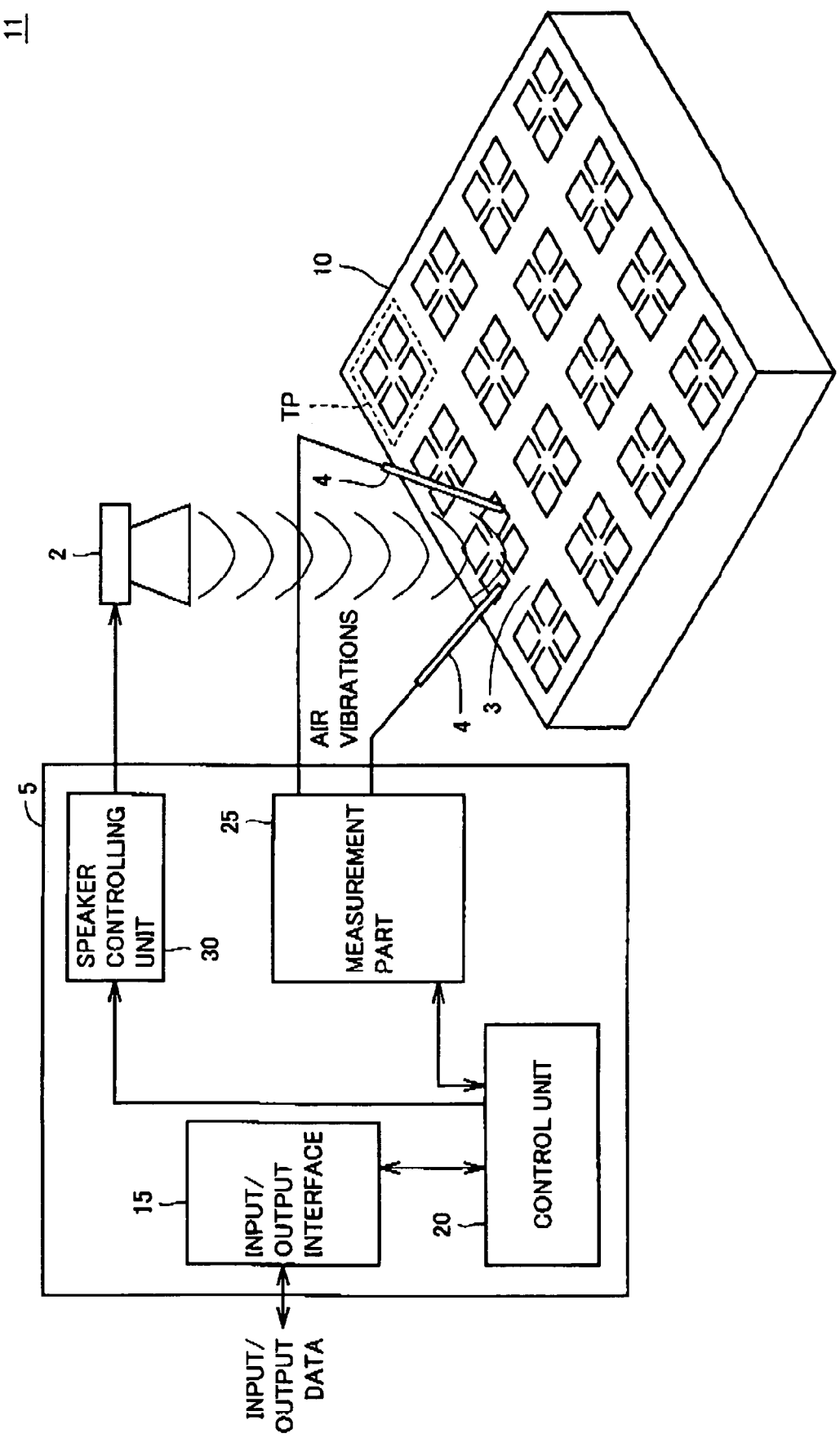
FIG. 11 is a schematic configuration diagram for illustrating a system for inspecting a micro structure according to a modification of the first embodiment of the present invention.

With reference to FIG. 11, inspection system 11 according to the modification of the first embodiment of the present invention is different from that of the first embodiment in the point where tester 5 is replaced with tester 6. Tester 6 is different from tester 5 in the point where microphone 3 and signal adjusting unit 35 are not present in tester 6. The other parts are the same, and the descriptions thereof are not repeated.

Figure 12:
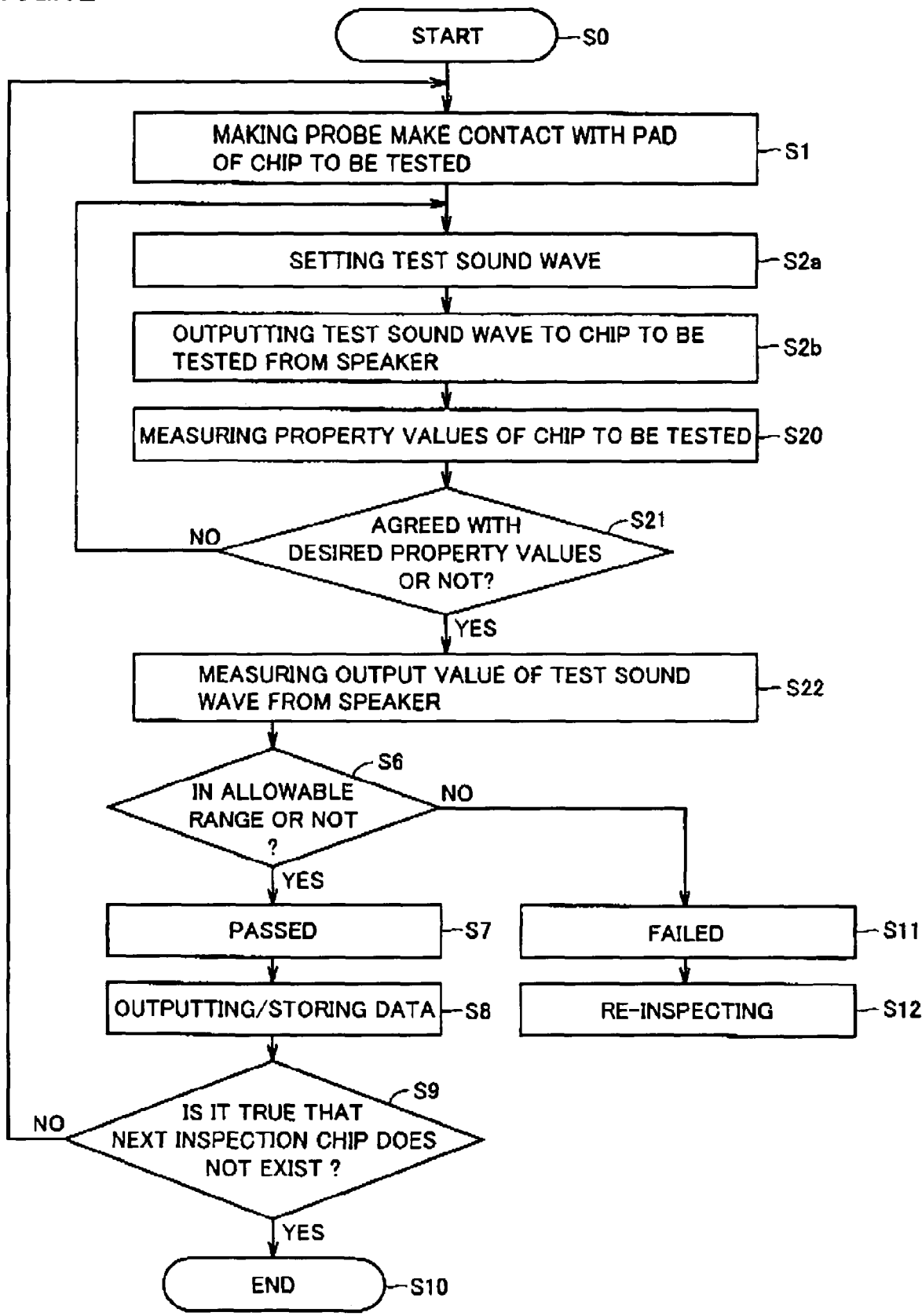
FIG. 12 is a flowchart for illustrating a method for inspecting a micro structure according to the modification of the first embodiment of the present invention.

With reference to the flowchart of FIG. 12, a method for inspecting a micro structure according to the modification of the first embodiment of the present invention is described.

With reference to FIG. 12, inspection (testing) of a micro structure is started as described above (step S0), and probe needles 4 are made to make contact with pads PD of chip to be tested TP (step S1). Next, test sound wave which is to be outputted from speaker 2 are set (step S2a), and then, test sound wave is outputted from speaker 2 to chip to be tested TP (step S2b).

Next, the property value of the chip to be tested is measured. Specifically speaking, the property value is measured by measurement part 25 on the basis of an electrical signal that is transmitted via prove needles 4, as described above (step S20).

Next, control unit 20 determines whether or not the property value that has been measured by measurement part 25, that is, measured data, coincides with a desired property value, that is, measured data (step S21).

Here, in the case where it is determined that the measured value does not coincide with a desired property value in step S21, the procedure again returns to step S2a, and test sound wave is reset. At this time, control unit 20 instructs speaker controlling unit 30 to correct test sound wave so that a desired property value is gained through chip to be tested TP as a result of measurement by measurement part 25. In response to an instruction from control unit 20, speaker controlling unit 30 microscopically adjusts the frequency and/or sound pressure of the test sound wave so that a desired property value can be gained, and thus, controls the system so that test sound wave is outputted from speaker 2 and a desired property is gained.

In the case where it is determined that the measured value coincides with a desired property value in step S21, the procedure goes to the next step S22, and the output value of the test sound wave that is outputted from speaker 2 is measured (step S22). Specifically speaking, control unit 20 acquires data on the sound pressure, frequency, voltage and the like of the test sound wave for gaining a desired property value when control unit 20 instructs speaker controlling unit 30 to output such test sound wave from speaker 2.

Next, control unit 20 determines whether or not the acquired data is in an allowable range (step S6). In step S6, in the case where it is determined that the data is in the allowable range, it is passed (step S7), while in the case where it is determined that the data is not in the allowable range, it is failed (step S11). The following procedures are the same as those described in the flowchart of FIG. 9 of the first embodiment, and the detailed descriptions thereof are not repeated.

A method for inspecting a micro structure according to the modification of the first embodiment of the present invention is a method for determining whether or not a chip to be tested has passed or failed, by comparing the level of the sound pressure or the like of predetermined test sound wave that has been set in advance and outputted from speaker 2 so that a predetermined property value detected from a passed chip, that is) a good product, can be gained, with the level of the sound pressure or the like of test sound wave that has been outputted so that this predetermined property value can be gained through the chip to be tested.

In the configuration according to the modification of the first embodiment of the present invention, tester 6, where microphone 3 and signal adjusting part 35 described in the first embodiment are not provided, can evaluate the property of a chip to be tested, and the cost of the tester can further be reduced by decreasing the number of parts.

Second Embodiment

An inspection method and an inspection device for implementing an inspection with higher precision are described according to a second embodiment of the present invention.

Figure 13:
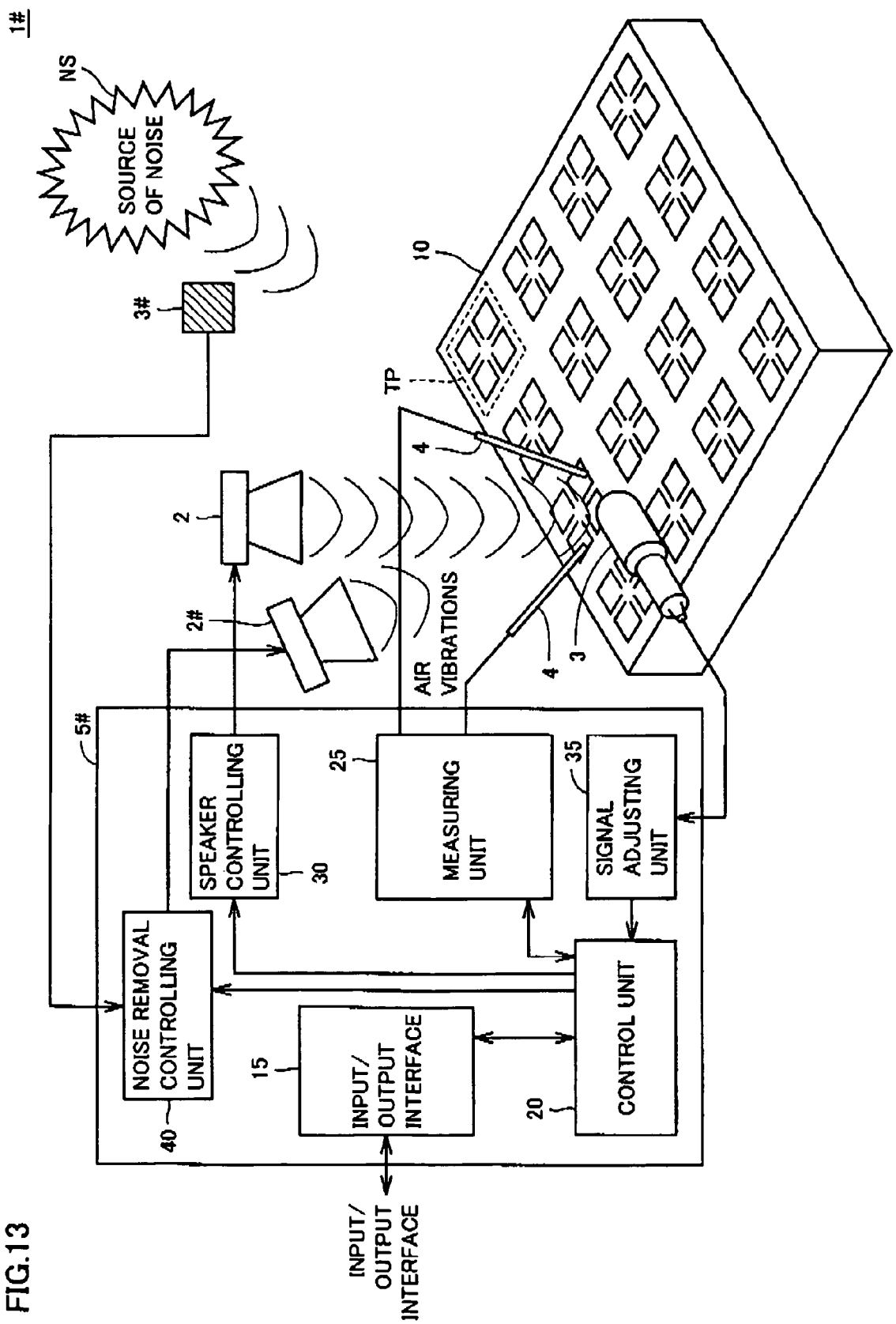
FIG. 13 is a schematic configuration diagram for illustrating a system for inspecting a micro structure according to a second embodiment of the present invention.

With reference to FIG. 13, an inspection system 1# according to the second embodiment of the present invention is different from inspection system 1 in the point where tester 5 has been replaced with tester 5#. Other parts are the same as in inspection system 1 that is described in FIG. 1, and therefore, the detailed descriptions thereof are not repeated.

According to the second embodiment of the present invention, in the case where there is a noise source NS at the time of testing, inspection with high precision is carried out by canceling noise sound wave that emanates from this noise source.

Tester 5# according to the second embodiment of the present invention is different from tester 5 in the point where tester 5# further includes a noise removal controlling unit 40, a speaker 2# and a microphone 3#. Other parts are the same, and the detailed descriptions thereof are not repeated.

Figure 14:
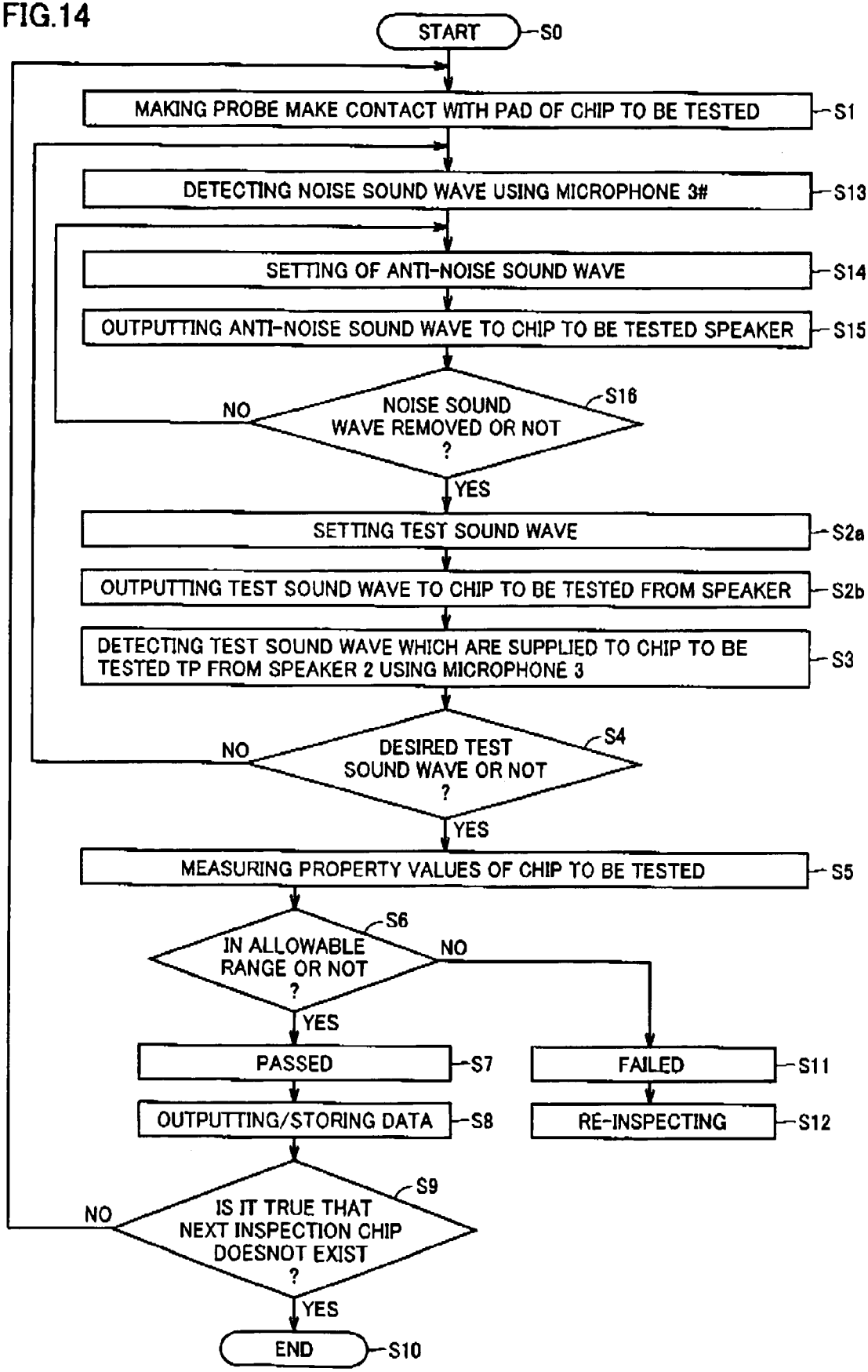
FIG. 14 is a flowchart for illustrating a method for inspecting a micro structure according to the second embodiment of the present invention.

With reference to the flowchart of FIG. 14, a method for inspecting a micro structure according to the second embodiment of the present invention is described.

Figure 15:
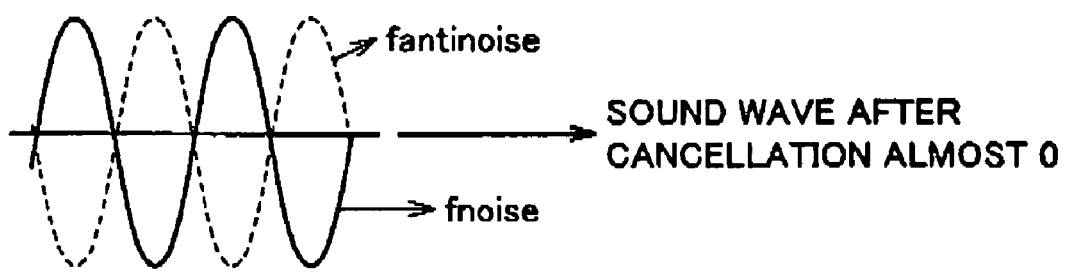
FIG. 15 is a diagram for illustrating synthesis of noise sound wave which is emitted from a noise source and anti-noise sound wave which is in phases exactly opposite to those of the noise sound wave.

With reference to FIG. 14, the method for inspecting a micro structure according to the second embodiment is different from the inspection method that is described in FIG. 9 in the point where steps S13 to S16 have further been added between steps S1 and S2a. Specifically speaking, in the step next to step S1, noise sound wave is detected using microphone 3# (step S13). Specifically speaking, microphone 3# detects noise sound wave that emanates from noise source NS and outputs the result thereof to noise removal controlling unit 40. Then, in response to an instruction from control unit 20, noise removal controlling unit 40 instructs speaker 2# to set anti-noise sound wave for canceling the noise sound wave that emanates from noise source NS (step S14), and to output the anti noise sound wave to chip to be tested TP from the speaker (step S15). Specifically speaking, anti-noise sound wave having the same frequency and the same sound pressure as those of noise sound wave and in phases opposite to the phases of the noise sound wave are outputted. As a result of this, as shown in FIG. 15, anti-noise sound wave "fantinoise" in phases exactly opposite to those of noise sound wave "fnoise" that emanates from noise source NS, for example, is outputted from speaker 2#, and thereby, noise sound wave "fnoise" is canceled so as to barely exist when they are synthesized and reach chip TP having a micro structure.

Then, control unit 20 determines whether or not noise sound wave has been removed on the basis of the output result from signal adjusting unit 35 via microphone 3 (step S16). In the case where it is determined that the noise sound wave have been removed, the procedure goes to the above-described next step S2a, and the following processes are the same as those described in FIG. 9, and the detailed descriptions thereof are not repeated.

Meanwhile, in the case where it is determined that noise sound wave has not been removed in step S16, the procedure again returns to step S14. That is, anti noise sound wave is reset. At this time, control unit 20 instructs noise removal controlling unit 40 to allow speaker controlling unit 30 to correct anti noise sound wave. In response to an instruction from control unit 20, noise removal controlling unit 40 microscopically adjusts the frequency and/or sound pressure and/or phases of the anti noise sound wave so that they become desired anti noise sound wave, and controls the system so that anti noise sound wave is outputted from speaker 2#.

In accordance with an inspection method and an inspection device according to the second embodiment of the present invention, noise can be removed or cancelled as a pre-process, before the output of test sound wave, and thus, inspection with high precision can be performed under conditions where there is no noise at the time of testing.

Here, it is also possible for the present example to have a configuration where a corrector and system are not specifically provided in advance in the case where desired test sound wave reaches the micro structure of a chip to be tested. Specifically speaking, processes up to steps S2a to S4 are carried out in advance before the start of testing, and a corrected control value for outputting desired test sound wave is stored in speaker controlling unit 30. Then, speaker controlling unit 30 controls an input to speaker 2 with this recorded control value at the time of actual testing of a micro structure, and thereby, it is possible to omit the above-described processes in steps S3 and S4 at the time of testing.

First Modification of Second Embodiment

Figure 16:
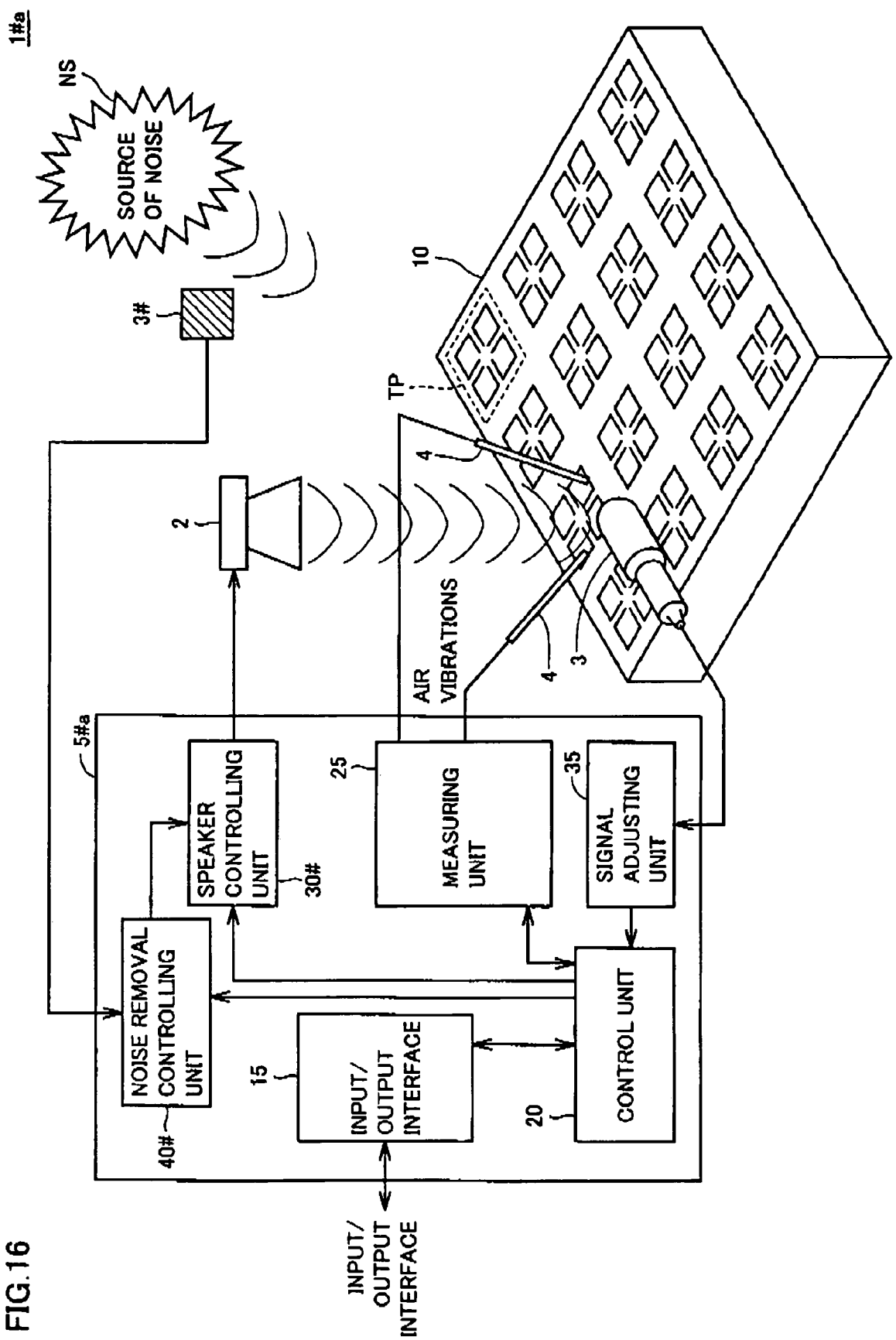
FIG. 16 is a schematic configuration diagram showing an inspection system according to a first modification of the second embodiment of the present invention.

With reference to FIG. 16, an inspection system 1#a according to a first modification of the second embodiment of the present invention is different from inspection system 1# that is described in FIG. 13 in the point where tester S# has been replaced with a tester 5#a. Specifically speaking, tester 5#a is different from tester 5# in the point where speaker 2# does not exist, and noise removal controlling unit 40 has been replaced with a noise removal controlling unit 40# and a speaker controlling unit 30#. Other parts are the same as in the inspection systems that are described in FIGS. 1 and 13, and therefore, the detailed descriptions thereof are not repeated.

Noise removal controlling unit 40# of tester 5#a according to the first modification of the second embodiment of the present invention instructs speaker controlling unit 30# to output the above-described anti-noise sound wave for removing noise sound wave that has been detected by microphone 3# from speaker 2. In response to an instruction from control unit 20 and noise removal controlling unit 40, speaker controlling unit 30# instructs the system to output anti noise sound wave together with test sound wave from speaker 2.

As a result of this, anti noise sound wave and test sound wave are generated using the same speaker 2, and the noise sound wave and the anti-noise sound wave cancel each other out, as described in FIG. 13, so that only the test sound wave reaches chip TP having a micro structure.

Anti noise sound wave and test sound wave are generated using speaker 2 as in the configuration according to the first modification of the second embodiment of the present invention, and thereby, the number of parts can further be reduced, so as to reduce cost.

Here, though in the configuration according to this embodiment, speaker controlling unit 30 outputs test sound wave which is sine wave having a single frequency from a speaker, the present invention is not limited to this, but rather, it is possible to synthesize sine wave signal having a number of different frequencies using, for example, an adder, not shown, and output the resulting signal from a speaker. As a result of this, responses to a number of frequencies can be detected at one time, and therefore, inspection of frequency response property as described in FIG. 10 can be efficiently and effectively performed. For example, if a frequency band to be inspected is divided into a high band and a low band and signals of single sine waves selected from the high and low bands, respectively, are composited together and thus output from the speaker and a signal responding thereto is divided by a band filter, responses to two frequencies can simultaneously be detected.

In addition, the test sound wave that is outputted from a speaker are not limited to a sine wave signal or a synthesized signal of sine wave signal, but rather, test sound wave having an arbitrary waveform, such as white noise, may be outputted using a function generator (generator of an arbitrary waveform), not shown. As a result of this, a micro structure exhibits a response that is dominated by the resonance of the moveable part, because white noise, for example, includes approximately the same amount of components of all frequencies, and the resonant frequency and vibration property of the micro structure can be easily inspected by detecting such a response. At this time, it is possible to use a band pass filter or the like to render the frequency band of the test sound wave a white noise limited to a region in the vicinity of the resonant frequency of the micro structure to perform inspection of resonance property of the micro structure efficiently and effectively.

Figure 32:
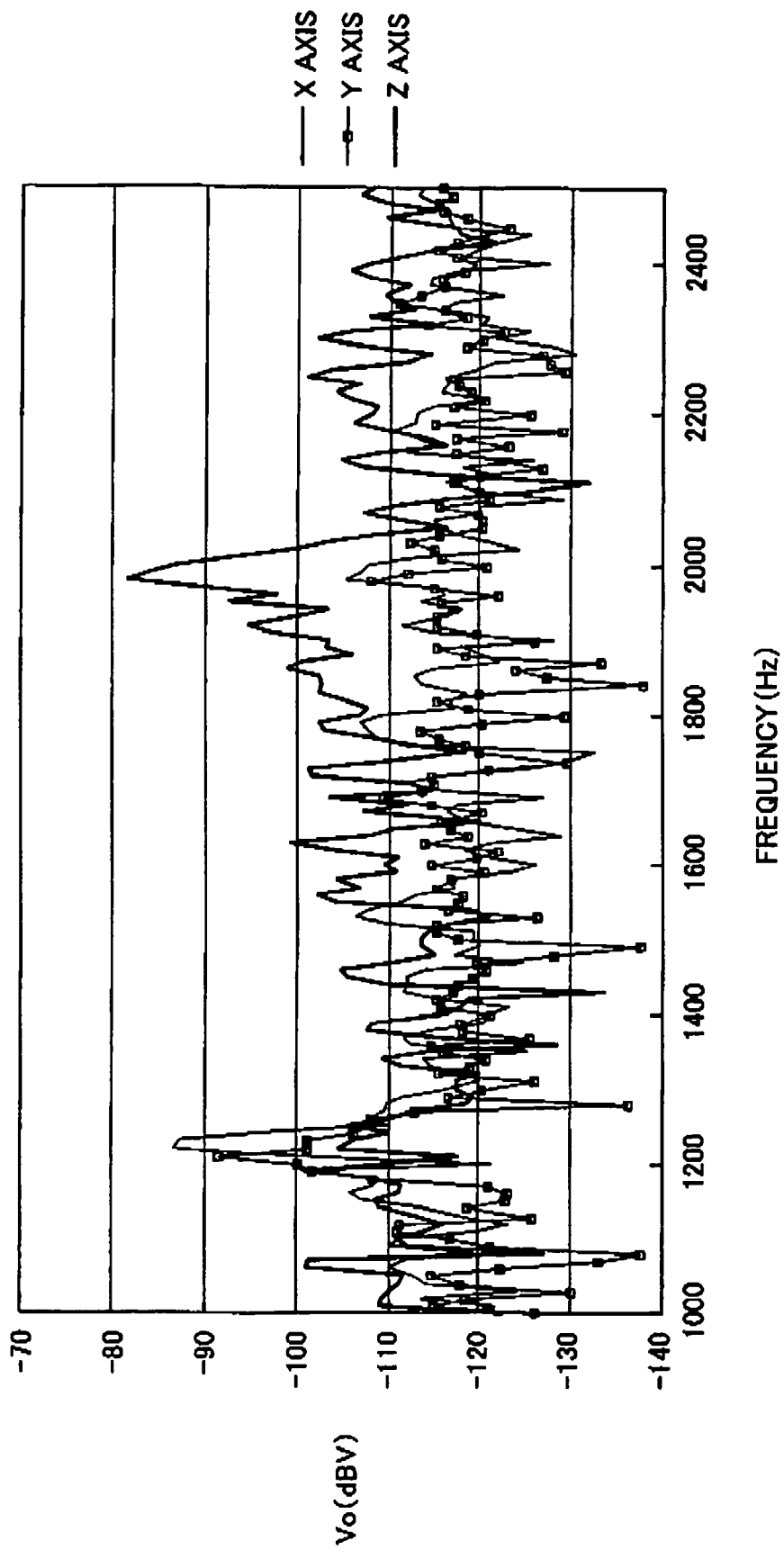
FIG. 32 is a graph representing a result of detecting responses of the three axes of the three-axis acceleration sensor simultaneously as a white noise of a frequency range is output as a test sound wave.

FIG. 32 is a graph representing a result of detecting responses of the three axes simultaneously as a white noise of a frequency range is output as a test sound wave. The test sound wave by the white noise is output and the three axis' output signals for a measurement time are each subjected to Fourier transform and plotted versus frequency. FIG. 32 shows a first measurement result. As can be seen from FIG. 32, there appear peaks representing resonant frequencies for the x, y and z axes, respectively. For the x and y axes, resonant frequencies around 1220-1240 Hz are indicated, and for the z axis, a resonant frequency around 1980 Hz is indicated. As the measurement time and the test sound wave's frequency band are limited, the input is a pseudo white noise, however resonant frequency and average output level can be evaluated. To more correctly inspect the micro structures property, a result of subjecting the test sound wave for the measurement time to Fourier transform is preferably used to normalize a frequency component of an output signal for each frequency. Furthermore such measurement may be done more than once and an average for each frequency may be provided. Furthermore If a moving average is provided for each appropriate frequency section and plotted in a graph, such crests and troughs as seen in FIG. 32 can be leveled to help to visually apprehend the property.

Second Modification of Second Embodiment

According to a second modification of the second embodiment of the present invention, a method for removing noise, that is, for noise cancellation, in a system that is different from the system for removing noise that is described in the above FIG. 14 is described.

Figure 17:
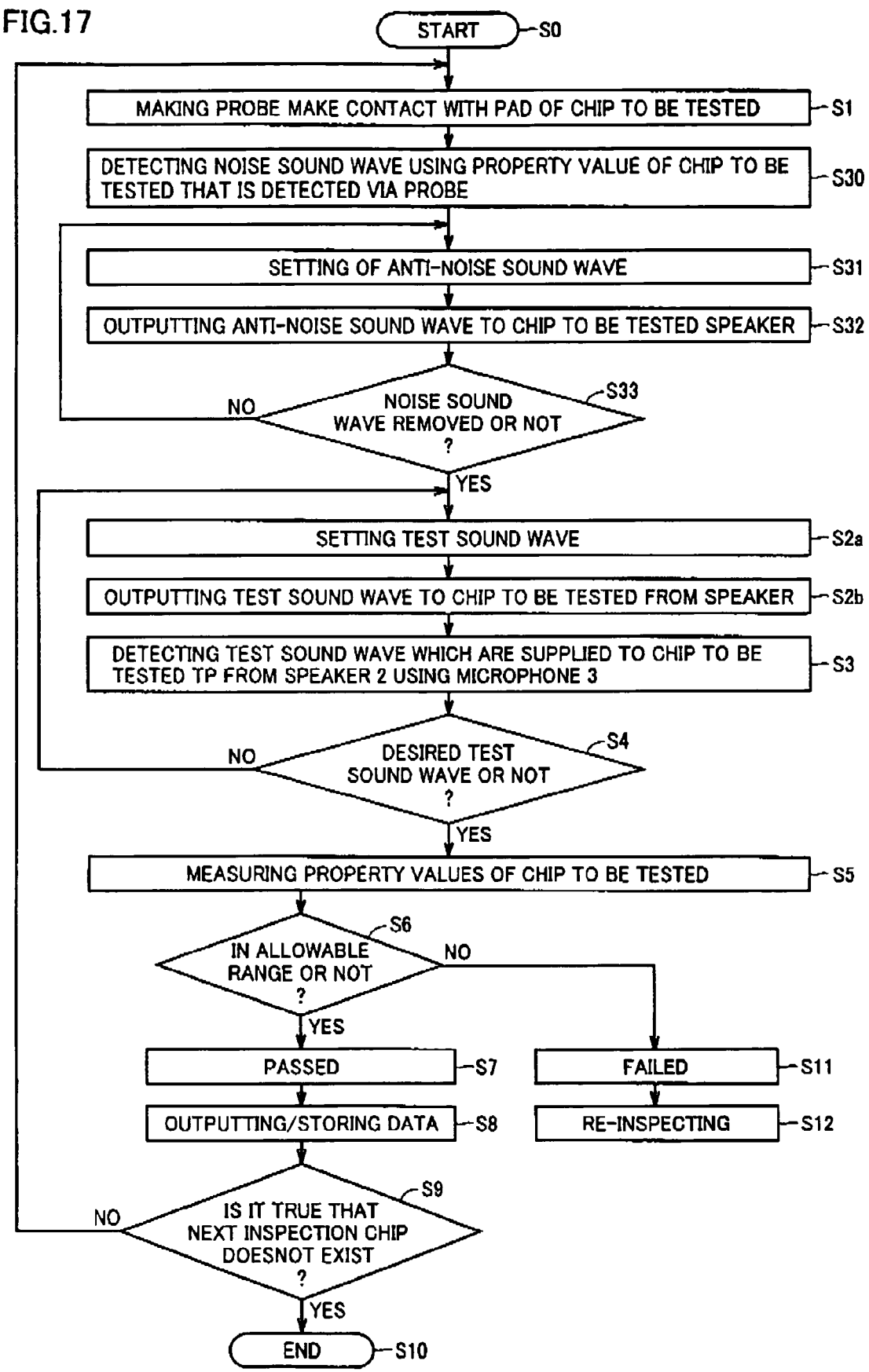
FIG. 17 is a flowchart for illustrating a method for inspecting a micro structure according to a second modification of the second embodiment of the present invention.

With reference to the flowchart of FIG. 17, a method for inspecting a micro structure according to the second modification of the second embodiment of the present invention is described.

With reference to FIG. 17, the present method is different from the inspection method that is described in FIG. 14 in the point where steps S13 to S16 are replaced with steps S30 to S33.

Specifically speaking, after step S1, noise sound wave is detected using the property value of a chip to be tested that is to be detected via probe needles (step S30). Specifically speaking, the probe needles are made to make contact with pads of the chip to be tested, and thereby, the moveable part is moved by noise sound wave or vibrations which are emitted from noise sound source NS, so that a predetermined property value is detected from the chip to be tested via the probe needles. Measurement part 25 outputs this result to control unit 20. Control unit 20 instructs noise removal controlling unit 40 to remove noise on the basis of the predetermined property value that has been measured by measurement part 25. Thus, in response to the instruction from control unit 20, noise removal controlling unit 40 sets anti-noise sound wave for canceling noise sound wave that is emitted from noise source NS in the speaker (step S31), and instructs chip to be tested TP to output anti-noise sound wave from the speaker (step S32). Specifically speaking, anti-noise sound wave which has the same frequency and the same sound pressure as the noise sound wave and which is in phases opposite to those of the noise sound wave is outputted. As a result of this, as described above, anti-noise sound wave "fantinoise" which is in phases exactly opposite to those of noise sound wave "fnoise" which is emitted from, for example, noise source NS, as shown in FIG. 16, are outputted from speaker 2#, and thereby, are synthesized, and noise sound wave "fnoise" is cancelled so as to be almost non-existent when the synthesized sound wave reaches chip TP of the micro structure.

In addition, control unit 20 determines whether or not the noise sound wave has been removed (step S33). Specifically speaking, it is determined whether or not a predetermined property value from the chip to be tested that is detected by measurement part 25 via the probe needles has become 0, that is, whether or not a predetermined property value has not been detected.

In the case where a predetermined property value has not been detected by measurement part 25 via the probe needles, that is, it is determined that noise sound wave has been removed, the procedure goes to the above-described next step S2a, and the following process is the same as that described in FIG. 9, and the detailed descriptions thereof are not repeated. Alternatively, it is also possible for the procedure to go to step S2a, where the following testing process is carried out in accordance with a system as described in FIG. 12.

Meanwhile, the procedure returns to step S31 again, in the case where it is determined in step S33 that the noise sound wave has not been removed. That is, anti-noise sound wave is reset. At this time, control unit 20 instructs noise removal controlling unit 40 to allow speaker controlling unit 30 to correct the anti-noise sound wave. In response to the instruction from control unit 20, noise removal controlling unit 40 microscopically adjusts the frequency and/or sound pressure and/or phases so that desired anti-noise sound wave can be gained, that is, a predetermined property value that is measured by measurement part 25 via the probe needles becomes 0 and controls the system so that the anti-noise sound wave is outputted from the speaker, In the inspection method according to the second modification of the second embodiment of the present invention also, in the same manner as in the inspection method according to the second embodiment and the first modification, noise can be removed, that is, canceled, as a pre-process before outputting test sound wave, and inspection with high precision can be performed in the state where there is no noise at the time of testing.

Furthermore, in the inspection method according to the second modification of the second embodiment of the present invention, it is not necessary to detect noise sound wave using a microphone, and thus, microphone 3# can be eliminated from the above-described testers 5# and 5#a, that is, the number of parts can be reduced, and the cost of the testers can be reduced.

In addition, the inspection method according to the second modification of the second embodiment of the present invention is a method for testing by outputting test sound wave after the property value of the chip to be tested that is detected via probe needles has been adjusted to 0 as a pre-process before outputting the test sound wave. That is, the present inspection method is a method for testing in the state where the effects of noise have been completely removed on the basis of the actual measurement result, and therefore, inspection with high precision can be performed in comparison with the methods which are described in the second embodiment and the first modification.

Though in the above-described embodiments, a three-axis acceleration sensor is described as an example of a micro structure, there are various types of MMS technologies, as described above, and the micro structure that is the object of the present technology is not limited to a multi-axial acceleration sensor. The present technology can be utilized for performance inspection of the operation property and mechanical property of an actuator and a microscopic mechanical part, as illustrated in the below.

Figure 18A:
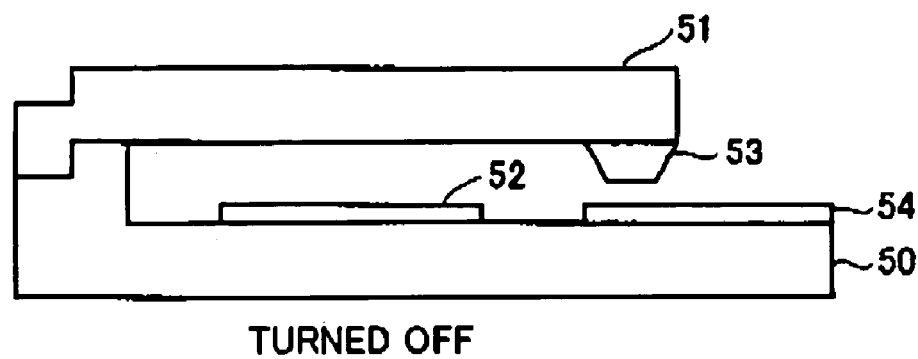
FIGS. 18A and 18B are conceptual diagrams for schematically illustrating a cantilever type MEMS switch.
Figure 18A:

FIG. 18A is a diagram for illustrating a case where a switch is stationary. With reference to FIG. 18A, an MEMS switch (hereinafter simply referred to as switch) is formed of a substrate 50, a cantilever 51, a control electrode 52, a cantilever joining part 53 and a joining electrode 54. In the state where no control signal is inputted, the switch does not operate.

Figure 18B:
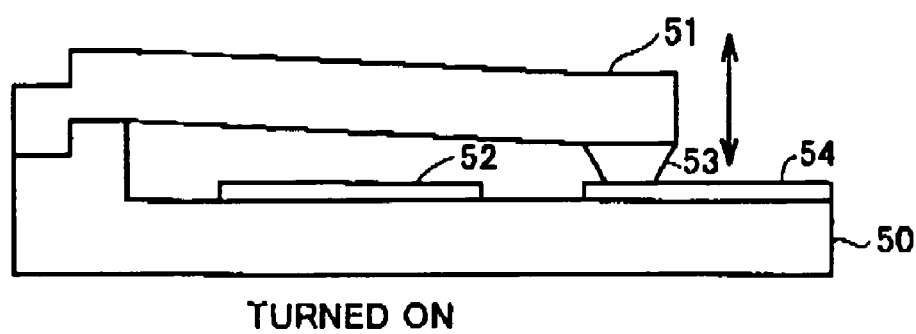

FIG. 18B is a diagram for illustrating a case where the switch operates. When a control signal is supplied to control electrode 52, cantilever 51 is attracted to the control electrode 52 side. As a result of this, cantilever joining part 53 makes contact with joining electrode 54. As a result of this, the switch becomes of the ON state. When a control signal in pulse form is supplied to control electrode 52, for example, cantilever joining part 53 moves upward and downward, repeating the joined state/non-joined state to joining electrode 54. This switch is microscopic, and is utilized as a switch for changing the frequency at high speed.

Figure 19A:
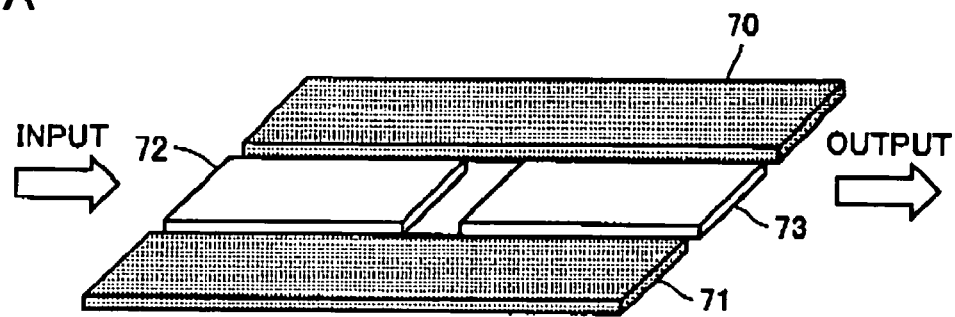
FIGS. 19A and 19B are conceptual diagrams for schematically illustrating an MEMS switch having a thin film membrane structure.
Figure 19B:
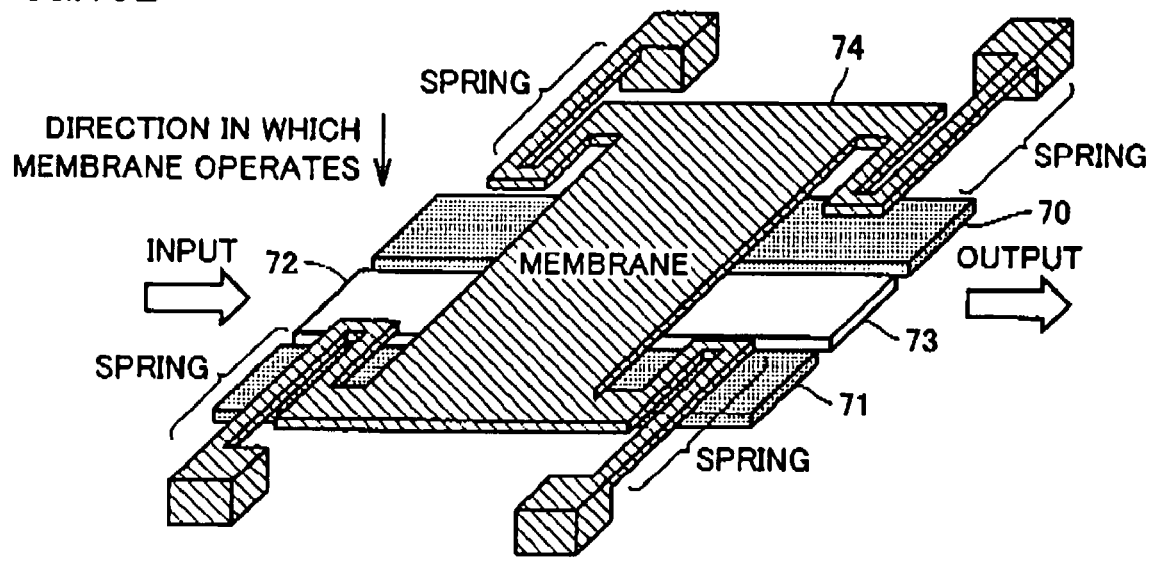

With reference to FIGS. 19A and 19B, an MEMS switch having a membrane structure of a thin film is schematically described.

FIG. 19A is a diagram for illustrating signal wires and electrodes.

With reference to FIG. 19A, a signal wire 72 into which a signal is inputted and a signal wire 73 from which a signal is outputted are shown. In addition, a trench is provided between the signal wires in the vicinity of the center portion, where an electrically insulated state is shown. In addition, electrodes 70 and 71 are provided on the two sides of the signal wires in the configuration.

FIG. 19B is a diagram for illustrating a case where the membrane structure is used as a switch. As shown in FIG. 19B, a membrane is placed above signal wires 72 and 73. Thin film beams form flexible springs. These support membrane 74. A driving voltage is applied to electrodes 70 and 71, and thereby, membrane 74 warps and is pulled down by electrostatic attraction, in a manner where the membrane makes contact with the signal wires which are provided beneath the membrane. As a result of this, the trench between the signal wires is filled in, providing the conductive state (ON). That is, the state where signal wires 72 and 73 are conductive is gained, so that an inputted signal is outputted. Meanwhile, in the case where the membrane and the signal wires do not make contact with each other, the state of non-conductivity (OFF) is gained.

Though an example where a membrane structure is used for a switch is described above, this membrane structure is not limited to a switch, but may also be a sensor part, such as a temperature sensor. In addition, the present technology makes it possible to perform performance inspection on a variety of mechanical parts, such as electron/ion transmitting thin films, using the property of a thin film or the illumination window of an electron beam illuminator, without moving the thin film portion, which is a moveable part of the membrane structure, at the time of utilization of the product.

Figure 20:
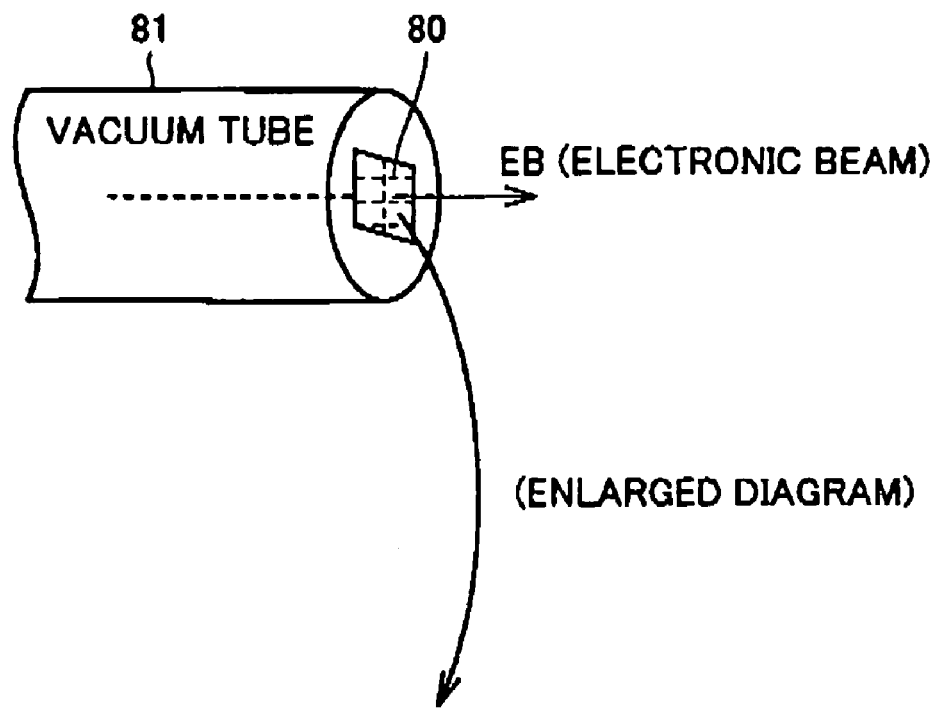
FIG. 20 is a diagram for illustrating a case where an illumination window of an electron beam illuminator has a membrane structure.
Figure 20:
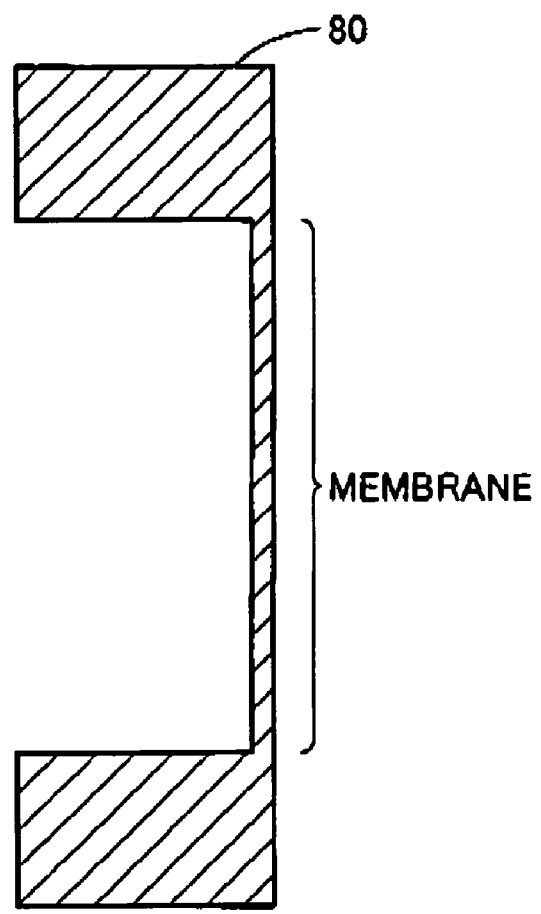

With reference to FIG. 20, a case is described where a membrane structure is used for the illumination window of an electron beam illuminator. As shown in FIG. 20, electron beam EB is emitted into the air from a vacuum tube 81 through an illumination window 80, and an enlarged cross section of a portion of illumination window 80 shows that a membrane structure is adopted in the thin film. Here, though FIG. 20 illustrates only one membrane structure where the membrane is formed of a single material, in some cases, the membrane may be formed of a number of materials so as to have a multi-layered film structure, or may be formed as an illumination window where a number of membrane structures are arranged in array form. In accordance with the technology of the present invention, it is possible to inspect the existence of damage or a crack in the film, or the film quality, even in a mechanical part that has a moveable part, as described above.

Figure 21A:
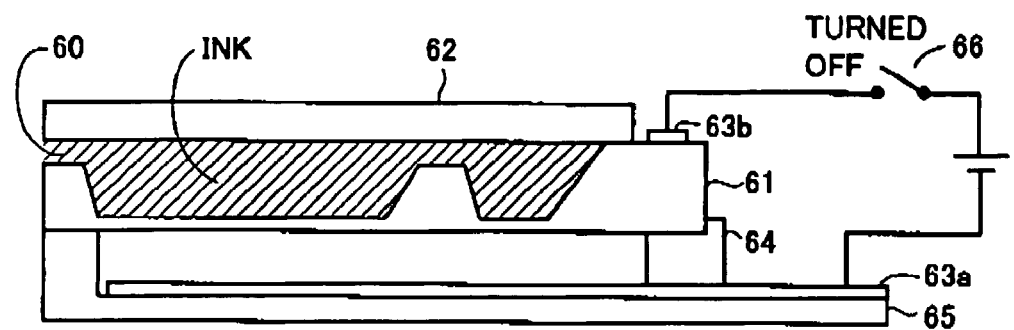
FIGS. 21A to 21C are schematic configuration diagrams for illustrating an ink jet printer head.
Figure 21B:
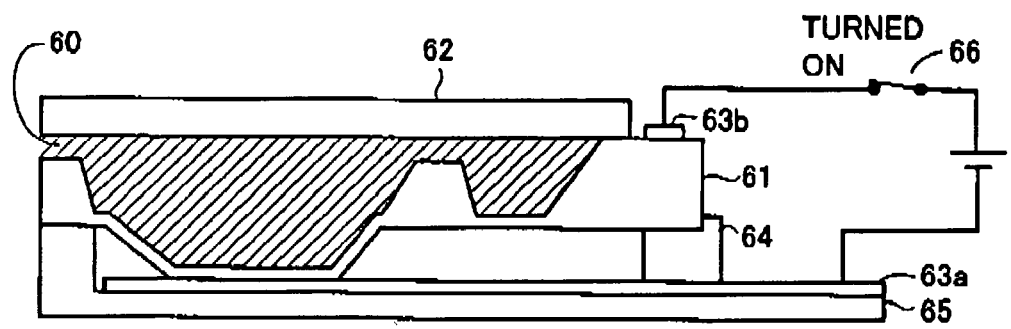
Figure 21C:
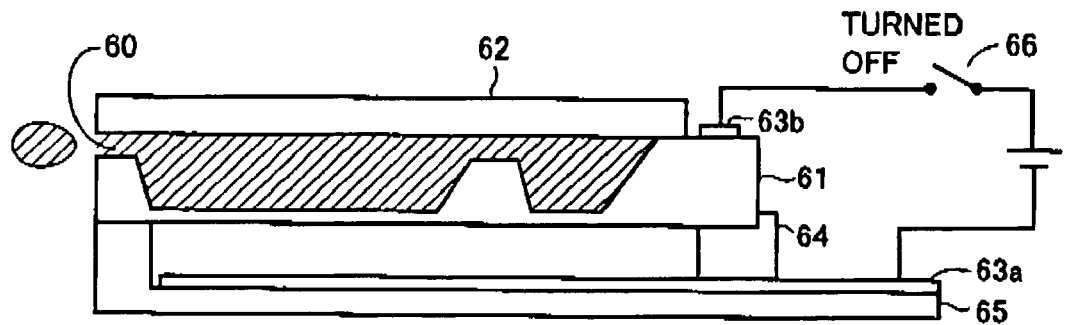

With reference to FIGS. 21A to 21C, an inkjet printer head is described.

FIG. 21A is a diagram for illustrating a case where an inkjet printer head is stationary. With reference to FIG. 21A, the inkjet printer head is formed of a nozzle 60, a piezoelectric actuator 61, a cover member 62, a support member 64 for supporting piezoelectric actuator 61, a control electrode 63a, a control electrode 63b that is joined to piezoelectric actuator 61, a substrate 65 and a switch 66. In the case where switch 66 is turned off, the inkjet printer head does not operate. Here, an ink is filled in between cover member 62 and piezoelectric actuator 61.

FIG. 21B is a diagram for illustrating a case where the inkjet printer head operates.

With reference to FIG. 21B, electrostatic attraction works between control electrode 63a and piezoelectric actuator 61 in the inkjet printer head when switch 66 is turned on. Along with this, piezoelectric actuator warps, as illustrated in the figure.

FIG. 21C is a diagram for illustrating a case where the switch is turned off after FIG. 21B.

As shown in FIG. 21C, piezoelectric actuator 61 that has been warped returns to its original state. At this time, a force of repulsion is gained, and thereby, the ink that fills the inside is jetted out from nozzle 60. This inkjet printer head operates as described above, and thereby, can be utilized as a microscopic and high-speed printer head.

When the inkjet printer head receives a sound wave of appropriate magnitude, piezoelectric actuator 61 deforms and electrostatic capacitance between control electrodes 63a and 63b varies. By detecting this variation the printer head can be inspected.

Figure 33A:
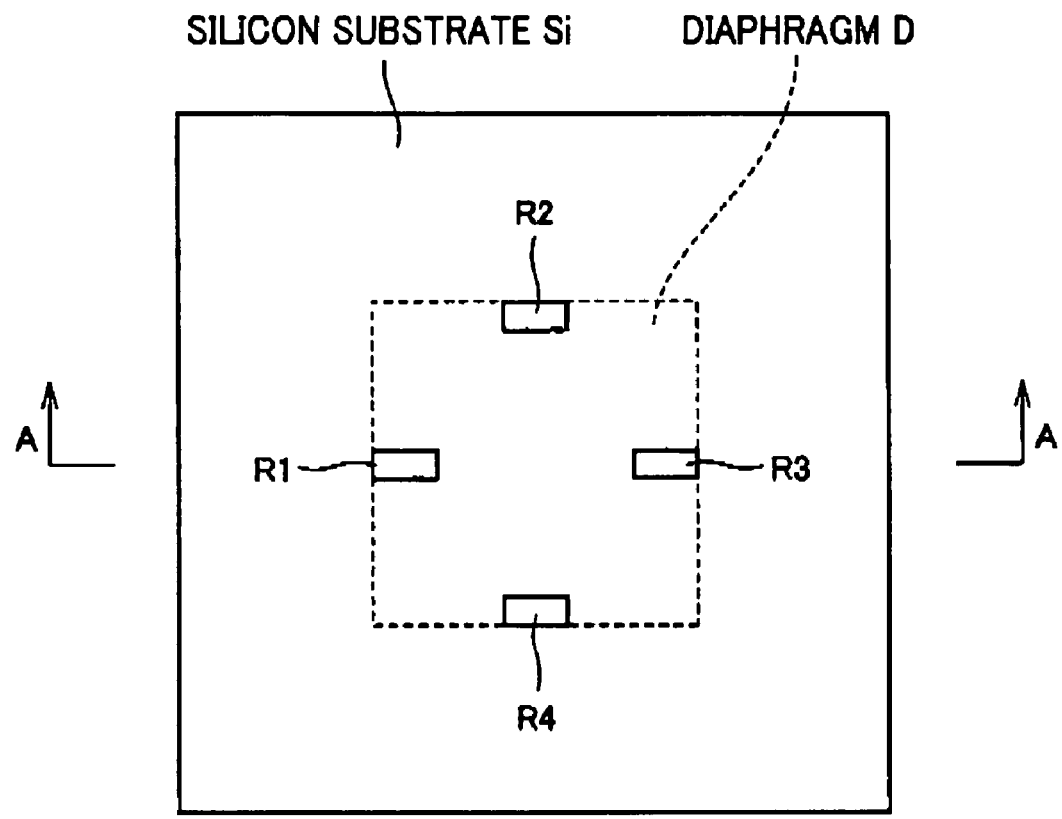
FIGS. 33A and 33B are a conceptual configuration diagram for illustrating a pressure sensor.
Figure 33B:
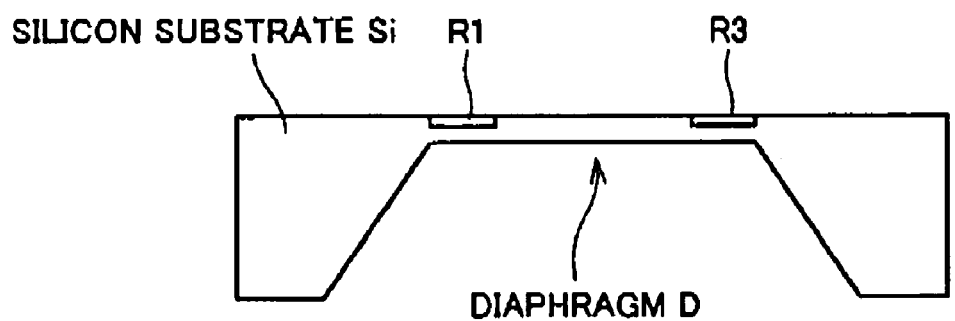

FIG. 33A is a plan view of a pressure sensor and FIG. 33B is a cross section taken along a line A-A of FIG. 33A. As shown in FIGS. 33A and 33B, a silicon substrate Si has a center provided with a diaphragm D substantially in a square and small in thickness. Diaphragm D has four sides having intermediate points with piezoelectric resistances R1, R2, R3, R4, respectively. When a difference between pressures exerted to opposite sides of diaphragm D causes the diaphragm to deform, a stress is caused in piezoelectric resistances R1-R4. The stress varies piezoelectric resistances R1-R4 in electrical resistance, and by detecting the variation the difference between pressures exerted to the opposite sides of diaphragm D can be measured.

The present method also allows the pressure sensor's operation to be confirmed such that the pressure sensor is formed on a substrate (for example a wafer). Exerting pressure to confirm operation entails causing a difference in pressure at opposite surfaces of a wafer, and it is difficult to perform inspection with the pressure sensor formed on the wafer.

It is also possible to perform inspection on these MEMS devices, such as an RF switch or an inkjet printer head, as described above, in accordance with the same system as that described above.

In accordance with the present invention if the above described acceleration sensor (or angular rate sensor) MEMS switch, membrane structure, inkjet printer head, pressure sensor and other similar movable part different in property are combined together to form a micro structure, e.g., if the acceleration sensor and the pressure sensor are combined together to form a single micro structure, such plurality of movable parts' properties can simultaneously be inspected. Furthermore, for MEMS technology, a substrate is often provided thereon with a plurality of micro structure, and the present method allows a plurality of micro structure on a substrate to be inspected simultaneously. Simultaneously inspecting a plurality of movable parts or those different in property or a plurality of micro structure allows an MEMS production process to be performed in a reduced period of time. Furthermore a substrate with a micro structure thereon can be inspected, and if a defective product is found it can be excluded from a subsequent packaging process and/or the like.

Third Embodiment

The systems as shown in the first and second embodiments are described as systems for inspecting the property of a micro structure by detecting an electrical signal that is outputted from the micro structure primarily by making probe needles make contact with pads of a chip having the micro structure.

In a third embodiment of the present invention, a system is specifically described where it is possible to inspect the property of a micro structure without directly using an electrical signal that is outputted from the micro structure. Specifically speaking, the system is described using the illumination window of an electron beam illuminator having a membrane structure.

Figure 22:
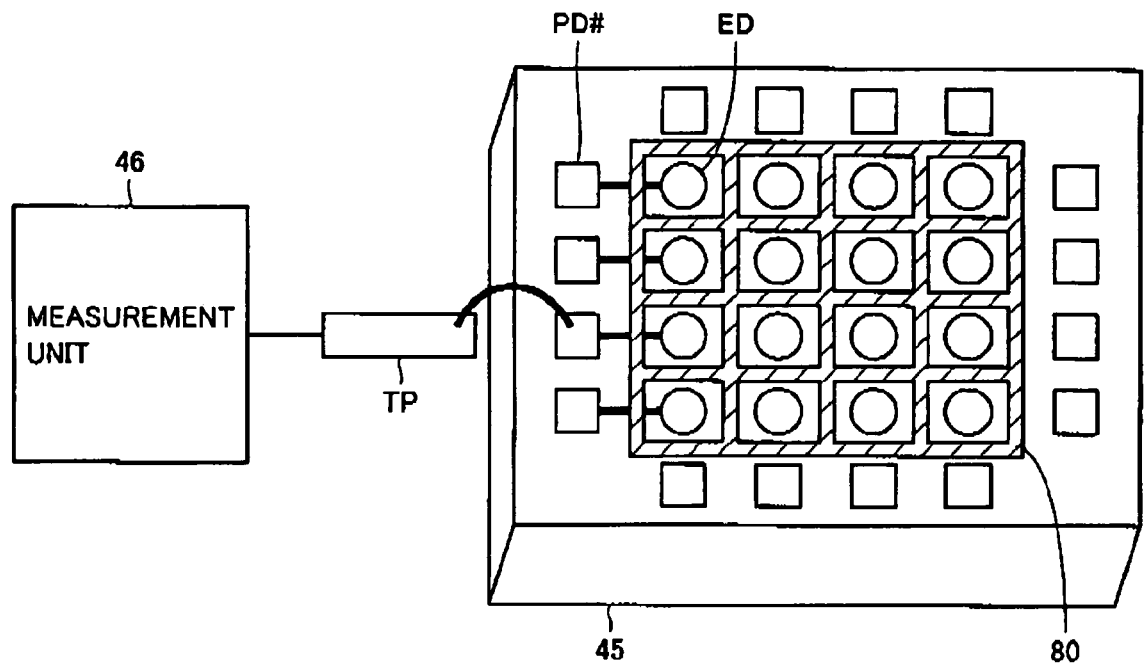
FIG. 22 is a conceptual diagram for illustrating a measurement part according to a third embodiment of the present invention.

With reference to FIG. 22, a measurement part 25# in accordance with the third embodiment of the present invention is described.

Specifically speaking, measurement part 25# in accordance with the third embodiment of the present invention includes a measurement unit 46 and a measurement jig 45. In addition, measurement unit 46 and measurement jig 45 are electrically coupled to each other via a terminal TP. Measurement unit 46 detects an electrostatic capacitance between an electrode ED and the object of measurement at the time of testing.

Measurement jig 45 includes a number of pads PD# which are provided in the periphery of the outer region, and a number of electrodes ED which are provided in the inner region thereof. Here, in the present example, one electrode ED is provided so as to correspond to one pad PD# from among the number of pads PD#, and these are electrically coupled to each other.

In addition, FIG. 22 shows a case where one pad PD# and terminal TP are electrically coupled to each other as an example.

In addition, the illumination window 80 of an electron beam illuminator having a membrane structure that is a micro structure is mounted on this measurement jig 45 as an example. Here, a tester of the third embodiment has a configuration where probe needles 4 have been removed and measurement part 25 which is the tester described in FIG. 1 is replaced with measurement part 25#, and other parts, such as the control unit and the speaker, have the same configuration, and therefore, the detailed descriptions thereof are not repeated.

Figure 23:
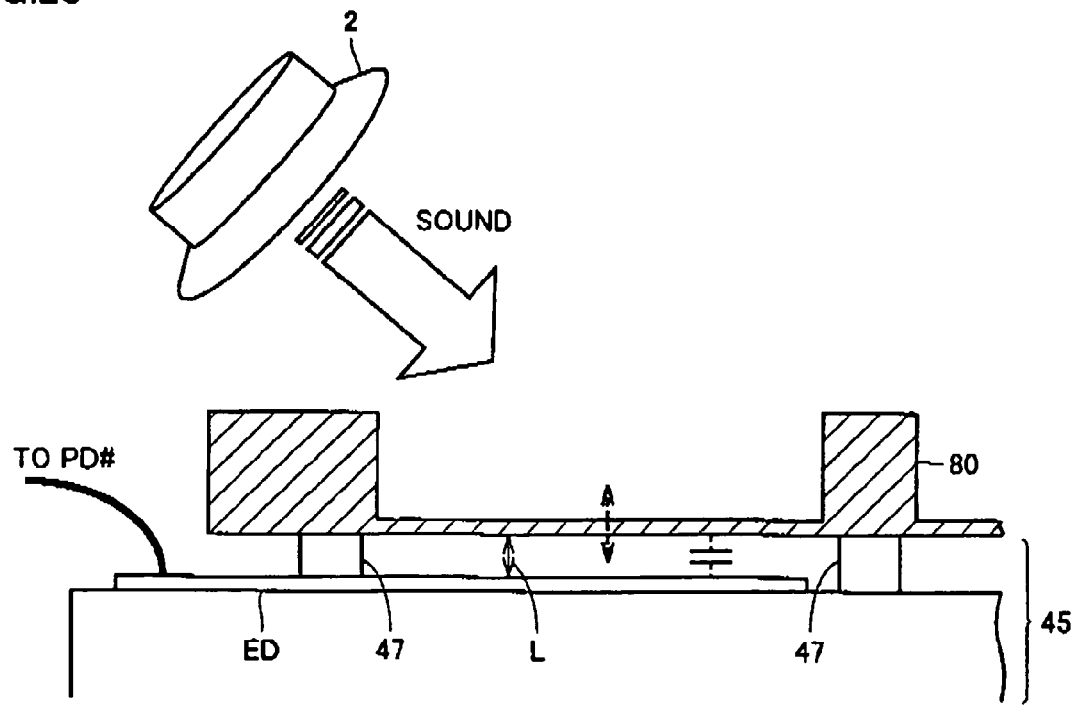
FIG. 23 is a diagram for illustrating in detail a measurement jig and an illumination window of an electron beam illuminator that is mounted on the measurement jig.

With reference to FIG. 23, measurement jig 45 and illumination window 80 of the electron beam illuminator that has been mounted on measurement jig 45 are described in detail.

With reference to FIG. 23, electrode ED is provided on the surface of measurement jig 45. Also, spacers 47 are provided so as to secure a predetermined space L between electrode ED and illumination window 80. In addition, electrode ED and external pad PD# are electrically coupled to each other, as described above.

Figure 24:
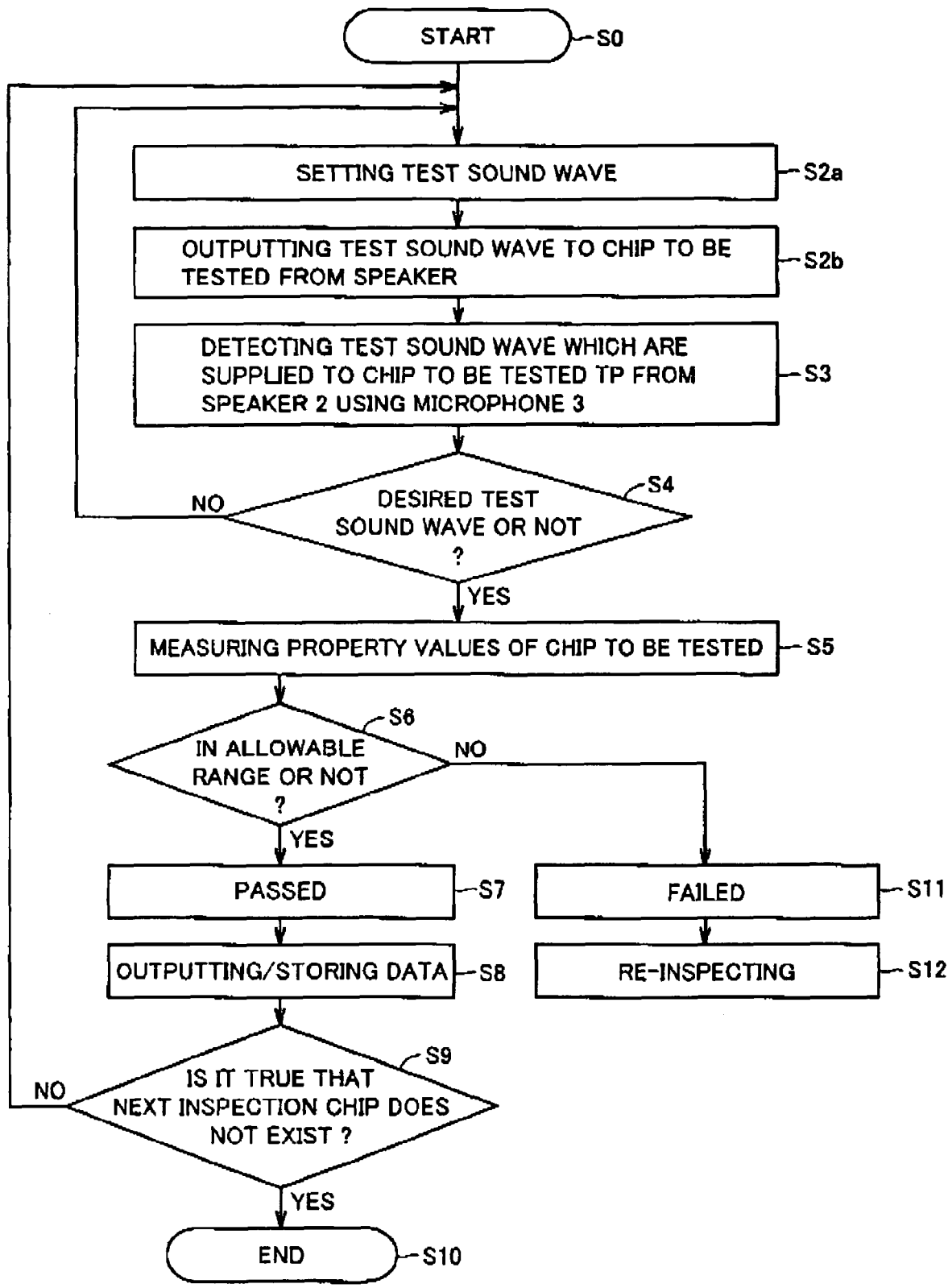
FIG. 24 is a flowchart for illustrating a method for inspecting a micro structure according to the third embodiment of the present invention.

With reference to the flowchart of FIG. 24, an inspection method for a micro structure according to the third embodiment of the present invention is described.

Inspection (testing) of a micro structure is started as described above (step S0). At this time, illumination window 80 of the electron beam illuminator having the micro structure that is the object of inspection is mounted on measurement jig 45. Next, test sound wave which is outputted from speaker 2 are set (step S2a), and then, test sound wave is outputted to illumination window 80 from speaker 2 (step S2b).

Next, the property value of the inspection chip is measured. In the present example, the electrostatic capacitance value that changes on the basis of the displacement of the moveable part that moves due to compression wave that is outputted from speaker 2 is measured by measurement unit 46 of measurement part 25# (step S5a).

Next, control unit 20 determines whether or not the property value that has been measured by measurement part 25#, that is, the measured data, has a desired property value, that is, is in an allowable range (step S6).

The following process is carried out in the same manner as described in FIG. 9, and therefore, the detailed descriptions thereof are not repeated.

The method for inspecting a micro structure according to the third embodiment of the present invention is not a method for inspecting the property of a micro structure on the basis of an electrical signal or the like that is directly gained from the micro structure due to the movement of the moveable part as described in FIG. 9, but rather, a method for inspecting property of the micro structure on the basis of a property value that is indirectly measured from the movement of the micro structure.

Figure 25:
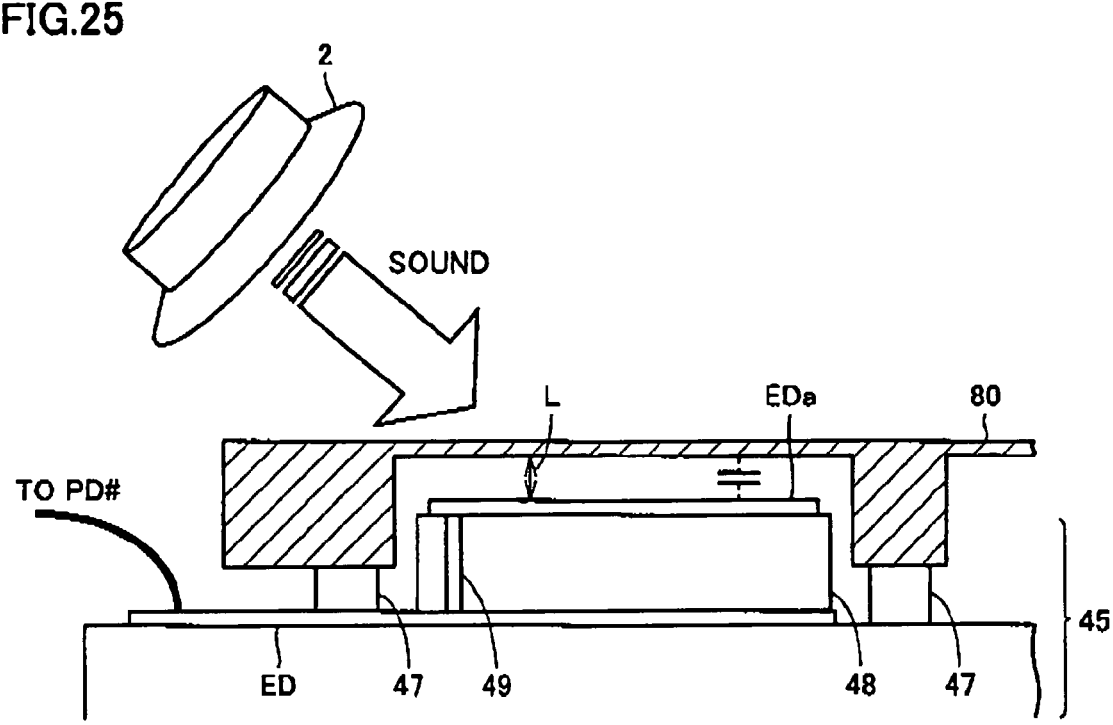
FIG. 25 is another diagram for illustrating in detail a measurement jig and an illumination window of an electron beam illuminator that is mounted on the measurement jig.

With reference to FIG. 25, measurement jig 45 and illumination window 80 of the electron beam illuminator that is mounted on measurement jig 45 are described in detail.

With reference to FIG. 25, illumination window 80 having the membrane structure that is shown in FIG. 25 is different from illumination window 80 shown in FIG. 23 in the point where illumination window 80 having the membrane structure that is shown in FIG. 23 is placed so as to face downward, while illumination window 80 having the membrane structure that is shown in FIG. 25 is placed so as to face upward. In addition, a spacer 48 and a sub electrode EDa are provided on top of electrode ED, and electrode ED and sub electrode EDa are electrically coupled to each other through a contact hole that goes through spacer 48. Also, as described in FIG. 23, the distance between the electrode, that is, sub electrode EDa, and the membrane structure is set at L.

Inspection of a micro structure can be performed, in the case of FIG. 25, in accordance with the same system as that described in FIG. 24.

In addition, the three-axis acceleration sensors of the above-described micro structure can also be inspected in accordance with the same system.

Figure 26:
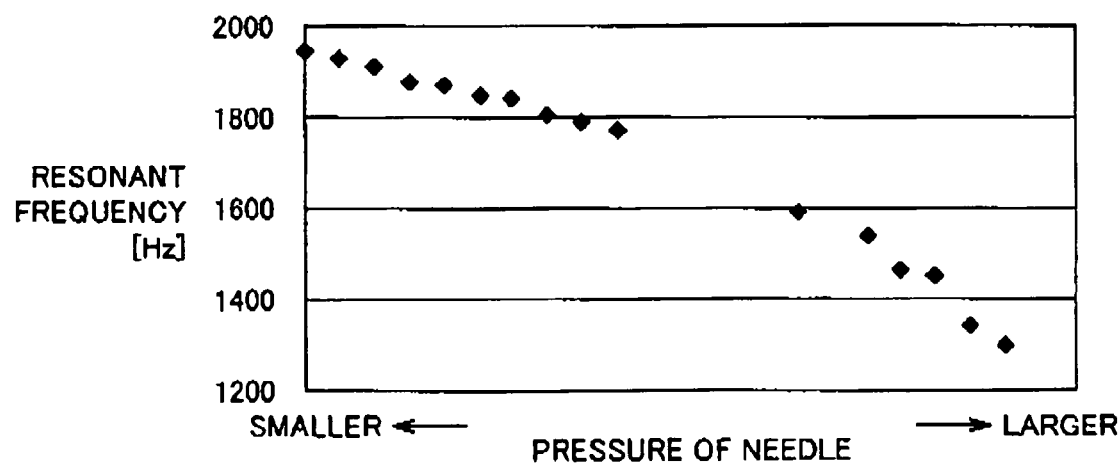
FIG. 26 is a graph for illustrating the resonant frequency at the time when probe needles are made to make contact with pads of a three-axis acceleration sensor.

With reference to FIG. 26, the resonant frequency at the time when probe needles are made to make contact with pads of a three-axis acceleration sensor is described. As shown in the present example, the greater the needle pressure of the probe needles which are made to make contact with pads is, the lower the resonant frequency tends to become. Accordingly, inspection can be easily performed without using probe needles and without changing the predetermined resonant frequency, by detecting and inspecting the electrostatic capacitance value that changes on the basis of the displacement of the moveable part that moves due to compression wave which is outputted from the above-described speaker.

Figure 27A:
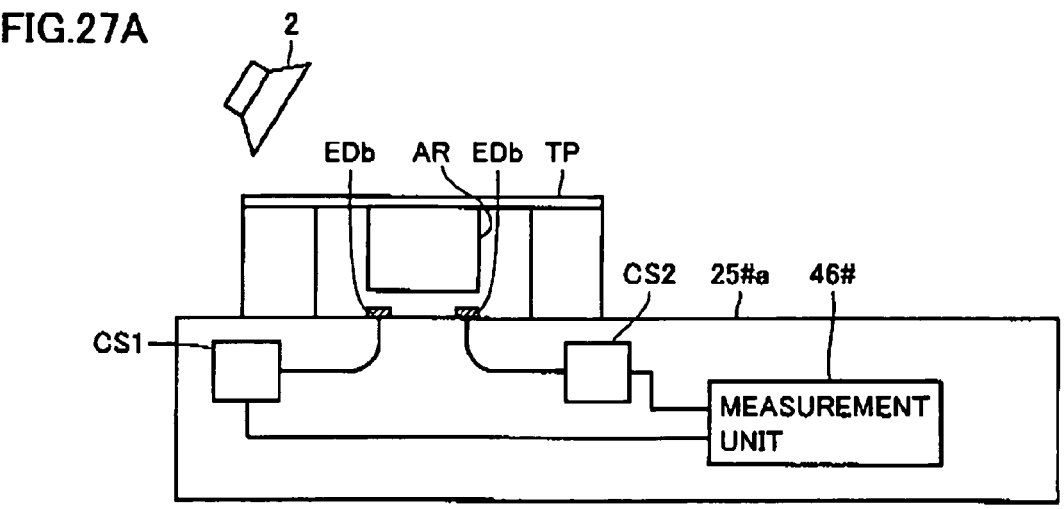
FIGS. 27A and 27B are conceptual diagrams for illustrating another measurement part according to the present invention.

With reference to FIG. 27A, here, a chip TP of a three-axis acceleration sensor is mounted on a measurement part 25#a. Measurement part 25#a includes capacitance detection circuits CS1 and CS2, electrode EDb and measurement unit 46#. Here, the tester of the present example has a configuration where probe needles 4 are removed and measurement part 25 of the tester that is described in FIG. 1 is replaced with measurement part 25#a in the same manner as described above, while other parts, such as the control unit and the speaker, have the same configuration, and therefore, the detailed descriptions thereof are not repeated.

Two electrodes EDb are provided beneath proof masses AR having a three-axis acceleration sensor, and are electrically coupled to capacitance detection circuits CS1 and CS2, respectively. In addition, capacitance detection circuits CS1 and CS2 are connected to measurement unit 46# so as to output the detected capacitance value, Measurement unit 46# measures the changing electrostatic capacitance value.

Figure 27B:
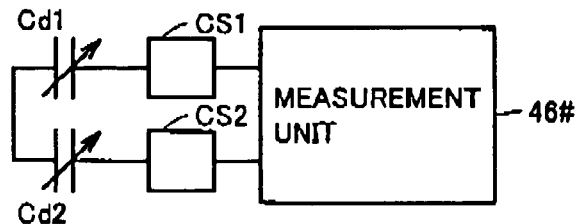

FIG. 27B is a circuit configuration diagram for illustrating capacitance detection in measurement part 25#a.

As shown in the present example, the initial values of electrostatic capacitances Cd1 and Cd2 between proof mass AR and electrode EDb are respectively detected by capacitance detection circuits CS2 and CS2. Then, the detection result are outputted to measurement unit 46#.

Figure 28A:
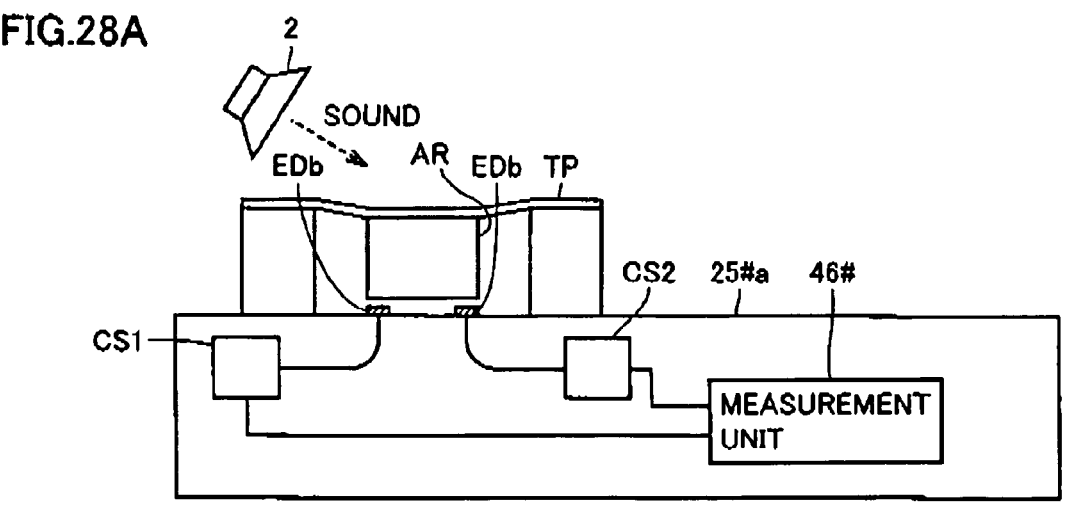
FIGS. 28A and 28B are diagrams for illustrating a case where the movable part of a chip is displaced.

With reference to FIG. 28A, proof mass AR, which is the moveable part, displaces due to compression wave from speaker 2.

Figure 28B:
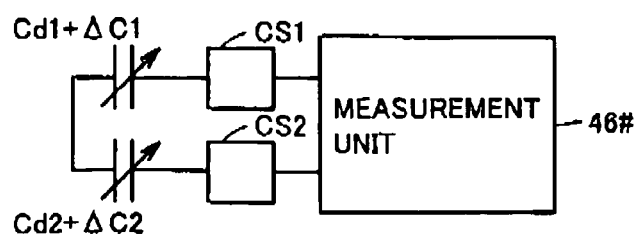

As shown in FIG. 28B, proof mass AR are displaced, and thereby, capacitance detection circuits CS1 and CS2 output the detected capacitance values to measurement unit 46#. In the present example, a case is shown where the electrostatic capacitance values are displaced from Cd1 to Cd1+ΔC1 and from Cd2 to Cd2+ΔC2, together with the displacement of the moveable part. These amounts of change are detected by measurement unit 46# and outputted to control unit 20, and thus, inspection of property of a three-axis acceleration sensor can be performed. Here, the method for inspecting a micro structure in this case is the same method as that described in the flowchart of FIG. 24, and therefore, the detailed descriptions thereof are not repeated.

Figure 29A:
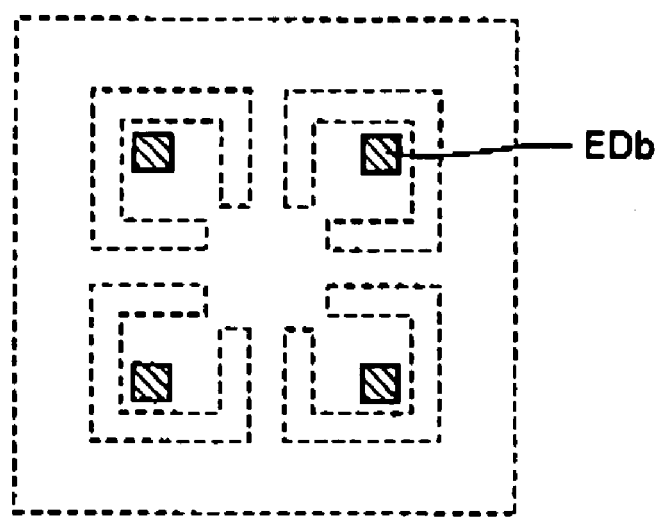
FIGS. 29A to 29C are diagrams for illustrating detection electrodes which are provided beneath a three-axis acceleration sensor.
Figure 29B:
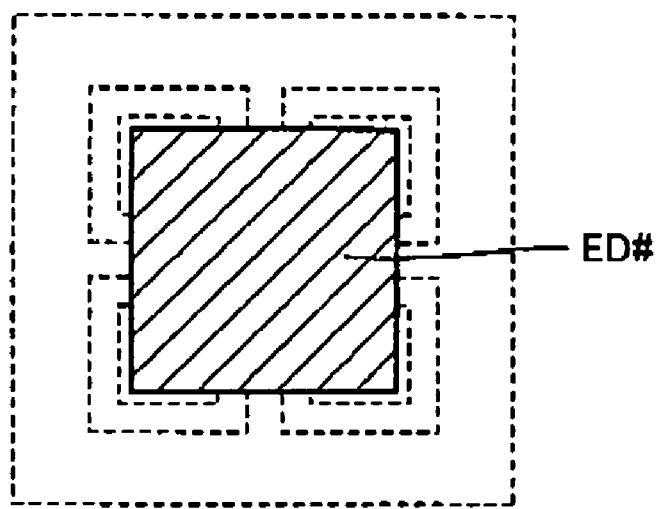
Figure 29C:
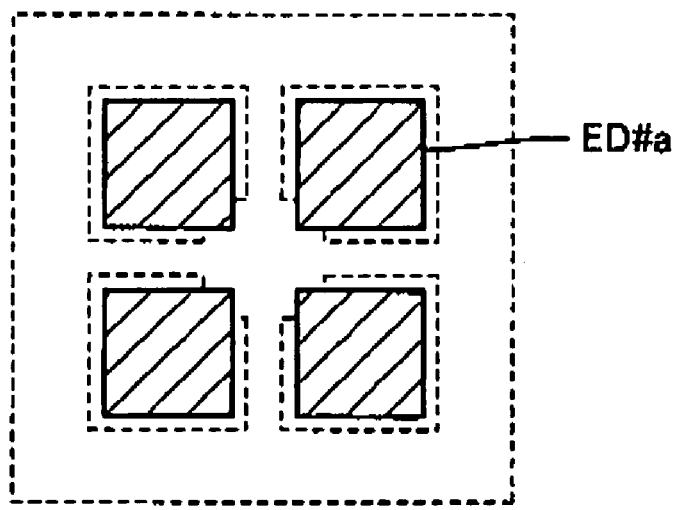

FIG. 29A shows a case where electrodes EDb are provided so as to correspond to proof masses AR, respectively, as described above, but it is also possible to perform inspection in accordance with the same system as that described above, by providing one electrode ED# corresponding to proof masses AR, as shown in FIG. 29B. Alternatively, as shown in FIG. 29C, it is also possible to perform inspection by providing electrodes ED#a, which are larger than the bottom areas of proof masses AR, in the present example, where the detection areas are greater than electrodes EDb that are shown in FIG. 29A Here, the system shown in FIG. 24 of the present specification is the same system as that in the case where step S1 that is described in FIG. 9 is removed from the first embodiment. That is, this is a system for evaluating property of a micro structure depending on whether or not desired property data has been detected in accordance with test sound wave which is supplied from speaker 2. In the same manner, it is also possible to evaluate the property in accordance with a system which is described in FIG. 12 of the modification of the first embodiment, FIG. 14 or FIG. 17 of the second embodiment or its modification, from which step S1 is removed. That is, it is also possible to carry out a desired test by adjusting test sound wave for gaining desired property data so as to evaluate the property of a micro structure depending on whether or not data such as the sound pressure of the gained test sound wave is within an allowable range, or by outputting anti-noise sound wave even in the case where noise sound wave or the like is generated. Here, it is possible to implement a tester by eliminating probe needles 4 in FIGS. 1, 11, 13 and 16, as described above, and by changing measurement part 25 to the above-described measurement part 25# or 25#a.

Here, it is also possible to supply sound wave which is compression wave so as to evaluate the property of the moveable part of a micro structure from the movement thereof with the naked eye. Alternatively, it is also possible to supply sound wave which is compression wave to a micro structure and to detect displacement in the movement of the moveable part of the micro structure using a so-called laser displacement meter, a displacement sensor or a proximity sensor so as to evaluate the property of the micro structure, by determining whether or not the detected amount of displacement is a desired amount of displacement by means of a determinator or the like.

Figure 30:
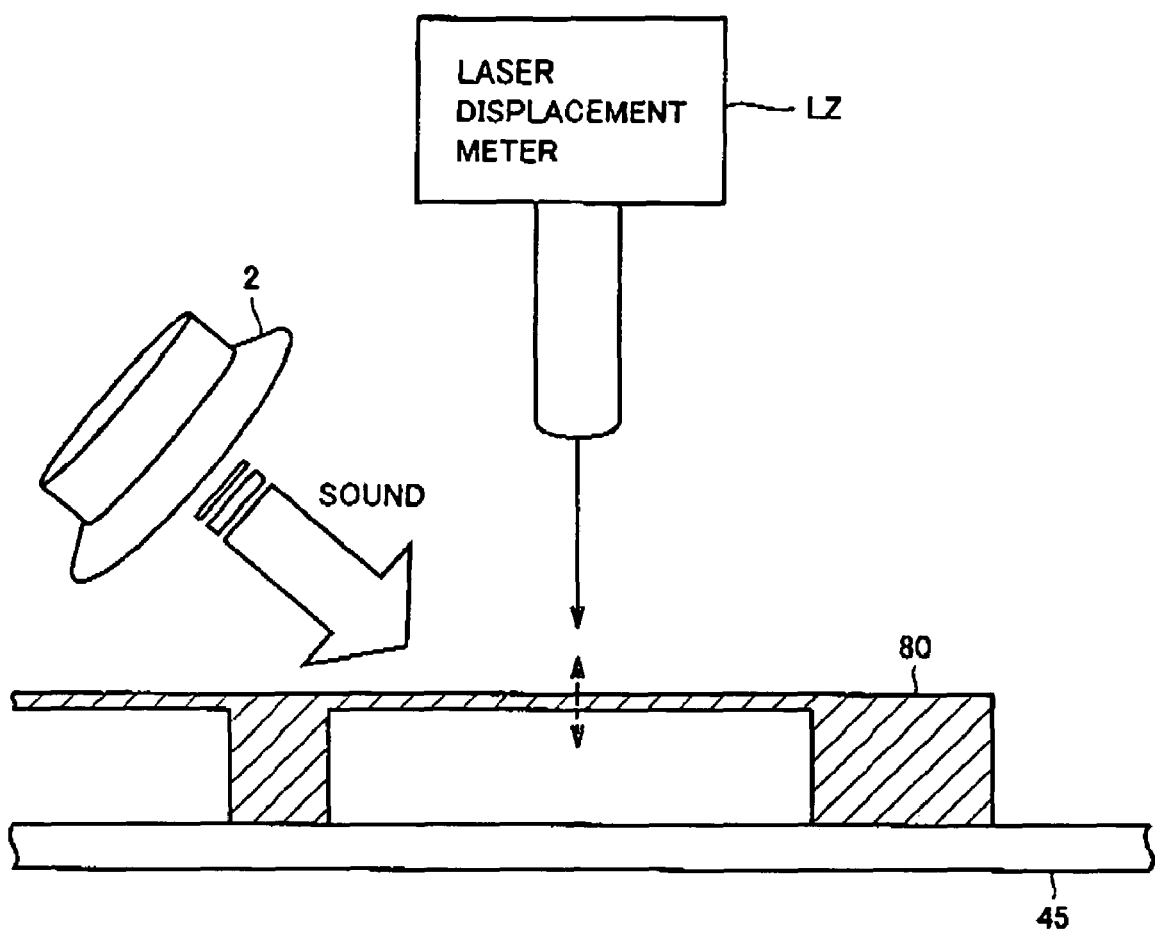
FIG. 30 is a diagram for illustrating a case where a displacement in the movement of the movable part of a micro structure is detected by a laser displacement meter which is a measurement part, and thereby, property of the micro structure are evaluated.

With reference to FIG. 30, a case is described where displacement in the movement of the moveable part of a micro structure is detected by means of a laser displacement meter LZ that is a measurement part, and thereby, the property of the micro structure are evaluated.

In this case also, property of illumination window 80 of an electron beam illuminator can be tested on the basis of whether or not a desired displacement has been detected.

Figure 31:
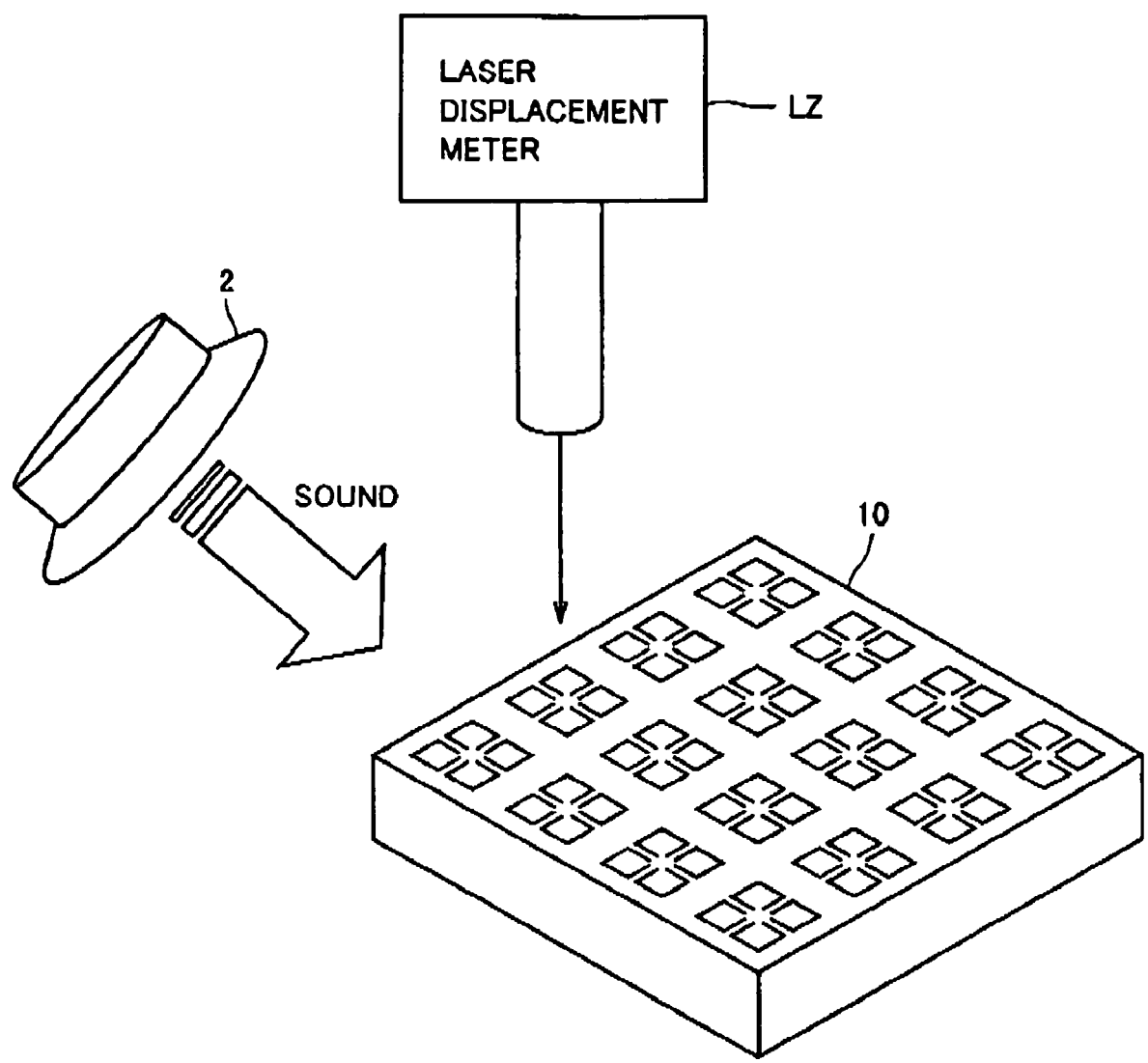
FIG. 31 is a diagram for illustrating a case where a displacement in the movement of the movable part of a an acceleration sensor is detected by a laser displacement meter which is a measurement part, and thereby, property of the acceleration sensor are evaluated.

In addition, it is also possible to test the property of an acceleration sensor, in addition to the illumination window of an electron beam illuminator, by detecting displacement in the movement of the moveable part of the acceleration sensor by means of a laser displacement meter LZ, which is a measurement part, as shown in FIG. 31.

The third embodiment also allows a plurality of movable parts or those different in property or a plurality of micro structure to be simultaneously inspected. Furthermore, a test sound wave in the form of white noise or that of a prescribed frequency range can be applied to a micro structure to eliminate the necessity of scanning the test sound wave's frequency in inspecting the micro structure's property.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A device for inspecting a micro structure which evaluates a property of at least one micro structure that has a movable part formed on a substrate, comprising:
   a sound wave generator for outputting a test sound wave to said micro structure at a time of testing
   a probe needle electrically connecting to an output pad provided at said micro structure, to extract a signal output from said micro structure configured on said substrate; and
   an evaluator for detecting the movement of the movable part of said micro structure in response to said test sound wave that has been outputted from said sound wave generator and for evaluating the property of said micro structure from a result of detecting via said probe needle said signal based on the movement of the movable part of said micro structure responding to said test sound wave output from said sound wave generator for outputting, with said probe needle in contact with said output pad.

2. The device for inspecting a micro structure according to claim 1, wherein
   a plurally of micro structure, each of which is the same as said micro structure, are arranged in an array form on the substrate.

3. The device for inspecting a micro structure according to claim 1, wherein said evaluator includes:
   a change amount detector for detecting an amount of change that changes in accordance with the movement of the movable part of said micro structure; and
   a determinator for evaluating the property of said micro structure on the basis of a comparison between the amount of change that has been detected by said change amount detector and the amount of change that becomes a predetermined threshold.

4. The device for inspecting a micro structure according to claim 3 wherein
   said change amount detector detects an amount of change in the impedance that changes in accordance with the movement of the movable part of said micro structure, and
   said determinator evaluates the property of said micro structure by comparing the amount of change in the impedance that has been detected by said change amount detector with the amount of change in the impedance that becomes a predetermined threshold.

5. The device for inspecting a micro structure according to claim 3, wherein
   said determinator evaluates the property of said micro structure by comparing the frequency that corresponds to the maximum amount of change that has been detected by said change amount detector with a desired frequency that corresponds to the amount of change that becomes a predetermined threshold.

6. The device for inspecting a micro structure according to claim 1, wherein
   said micro structure corresponds to at least one of an acceleration sensor and an angular rate sensor.

7. The device for inspecting a micro structure according to claim 6, wherein
   said acceleration sensor and angular rate sensor respectively correspond to a multi-axial acceleration sensor and multi-axial angular rate sensor.

8. A device for inspecting a micro structure which evaluates a property of at least one micro structure that has a movable part formed on a substrate, comprising:
a sound wave generator for outputting a test sound wave to said micro structure at a time of testing and
an evaluator for detecting the movement of the movable part of said micro structure in response to said test sound wave that has been outputted from said sound wave generator and for evaluating the property of said micro structure on the basis of the detection result, wherein
said evaluator includes:
a position displacement detector for detecting an amount of displacement of the movable part of said micro structure that displaces in accordance with the movement of the movable part of said micro structure; and
a determinator for evaluating the property of said micro structure on the basis of a comparison between the amount of displacement that has been detected by said position displacement detector and the amount of displacement that becomes a predetermined threshold.

9. The device for inspecting a micro structure according to claim 8, wherein
said position displacement detector detects an electrostatic capacitance that changes in accordance with the movement of the movable part of said micro structure, and
said determinator evaluates the property of said micro structure by comparing the electrostatic capacitance that has been detected by said position displacement detector with the electrostatic capacitance that becomes a predetermined threshold.

10. The device for inspecting a micro structure according to claim 8, wherein
said position displacement detector detects an amount of displacement on the basis of the movement of the movable part of said micro structure by using a laser.

11. The device for inspecting a micro structure according to claim 8, wherein
said determinator evaluates the property of said micro structure by comparing the frequency that corresponds to the maximum amount of displacement that has been detected by said position displacement detector with a desired frequency that corresponds to the amount of displacement that becomes a predetermined threshold.

12. A device for inspecting a micro structure which evaluates a property of at least one micro structure that has a movable part formed on a substrate, comprising:
a sound wave generator for outputting a test sound wave to said micro structure at a time of testing, wherein
the movement of the movable part of said micro structure is detected in response to said test sound wave that has been outputted from said sound wave generator, and the property of said micro structure is evaluated on the basis of the detection result, and
said sound wave generator includes:
a sound wave outputting part for outputting said test sound wave having a sound pressure in accordance with an input from the outside;
a detector for detecting test sound wave that reaches the proximity of said micro structure; and
a sound wave corrector for correcting the test sound wave that has been outputted from said sound wave outputting part by comparing the sound pressure level of the test sound wave that has been detected by said detector with the sound pressure level of the predetermined test sound wave that becomes a reference.

13. The device for inspecting a micro structure according to claim 12, wherein
said sound wave generator further includes a noise remover for removing a noise sound wave that reaches said micro structure from the outside.

14. The device for inspecting a micro structure according to claim 12, wherein
said noise remover outputs an anti-noise sound wave which is in phases opposite to those of said noise sound wave so as to cancel said noise sound wave on the basis of said noise sound wave that has been detected by said detector before testing and which have the same frequency and sound pressure as those of said noise sound wave.

15. The device for inspecting a micro structure according to claim 14, wherein
said anti-noise sound wave is output from said sound wave outputting part together with said test sound wave at the time of said testing.

16. The device for inspecting a micro structure according to claim 12, wherein
said evaluator outputs the result determined by said determinator upon receiving the detection result of the test sound wave that has been detected by said detector of said sound wave generator.

17. A device for inspecting a micro structure which evaluates property of at least one micro structure that has a movable part formed on a substrate comprising:
a sound wave generator for outputting a test sound wave to said micro structure at a time of testing, and
an evaluator for detecting the movement of the movable part of said micro structure in response to said test sound wave that has been outputted from said sound wave generator and for evaluating the property of said micro structure on the basis of the detection result, wherein
said evaluator includes:
an electrostatic capacitance detection electrode that has been installed so as to face the moveable part of said micro structure;
a capacitance detector for detecting the electrostatic capacitance between said electrostatic capacitance detection electrode and the movable part of said micro structure that changes in accordance with the movement of the movable part of said micro structure; and
a determinator for evaluating the property of said micro structure on the basis of a comparison between the electrostatic capacitance that has changed and has been detected by said capacitance detector and the electrostatic capacitance that becomes a predetermined threshold.

18. A device for inspecting an micro structure which evaluates a property of at least one micro structure that has a movable part formed on a substrate, comprising:
a sound wave generator for outputting a test sound wave to said micro structure at a time of testing, wherein
the movement of the moveable part of said micro structure is detected in response to said test sound wave that has been outputted from said sound wave generator, and the property of said micro structure is evaluated on then the basis of the detection result, and at least two movements of said movable part of said micro structure are simultaneously detected and a resultant detection is used to evaluate at least two properties of said micro structure simultaneously.

19. The device for inspecting a micro structure according to claim 18, wherein movements in at least two directions of said movable part of said micro structure are simultaneously detected and a resultant detection is used to evaluate properties in at least two directions of said micro structure simultaneously.

20. The device for inspecting a micro structure according to claim 18, wherein when said micro structure has at least two movable parts and/or said substrate has at least two micro structure thereon, said at least two movable parts' respective movements are simultaneously detected and a resultant detection is used to evaluate simultaneously properties of said at least two movable parts, respectively, of said micro structure or said at least two micro structure.

21. The device for inspecting a micro structure according to claim 20, wherein when said at least two movable parts have different property, respectively, in movability, said at least two movable parts' respective movements are simultaneously detected and a resultant detection is used to simultaneously evaluate properties of said at least two movable parts, respectively, having different properties, respectively, in movability.

22. A device for inspecting a micro structure which evaluates property of at least one micro structure that has a movable part formed on a substrate, comprising:
    a sound wave generator for outputting a test sound wave to said micro structure at a time of testing, wherein
    the movement of the movable part of said micro structure is detected in response to said test sound wave that has been outputted from said sound wave generator, and the property of said micro structure is evaluated on then the basis of the detection result, and said sound wave generator outputs as said test sound wave a composite wave including at least two sound waves different in frequency.

23. The device for inspecting a micro structure according to claim 22, wherein said sound wave generator outputs white noise as said test sound wave.

24. The device for inspecting a micro structure according to claim 22, wherein said sound wave generator outputs as said test sound wave a white noise in a prescribed frequency range.

25. A method for inspecting a micro structure, comprising the steps of:
    supplying a test sound wave to at least one micro structure that has a movable part formed on a substrate;
    connecting electrically a probe needle to an output pad provided at said micro structure, to extract a signal output from said micro structure configured on said substrate;
    detecting the movement of the movable part of said micro structure in response to said test sound wave; and
    evaluating a property of said micro structure from a result of detecting via said probe needle said signal based on the movement of the movable part of said-micro structure responding to said test sound wave.

26. The method for inspecting a micro structure according to claim 25, wherein:
    the step of detecting detects simultaneously at least two movements of said movable part of said micro structure; and
    the step of evaluating evaluates simultaneously at least two properties of said micro structure.

27. The method for inspecting a micro structure according to claim 25, wherein the step of supplying supplies a white noise as said test sound wave.

28. A program for inspecting a micro structure which allows a computer to implement a method for inspecting a micro structure, comprising the steps of:
    supplying a test sound wave to at least one micro structure that has a movable part formed on a substrate;
    connecting electrically a probe needle to an output pad provided at said micro structure, to extract a signal output from said micro structure configured on said substrate;
    detecting a movement of the movable part of said micro structure in response to said test sound wave; and
    evaluating a property of said micro structure from a result of detecting via said probe needle said signal based on the movement of the movable part of said micro structure responding to said test sound wave.

29. The program according to claim 28, wherein:
    the step of detecting detects simultaneously at least two movements of said movable part of said micro structure; and
    the step of evaluating evaluates simultaneously at least two properties of said micro structure.

30. The program according to claim 28, wherein the step of supplying supplies white noise as said test sound wave.

* * * * *

UNITED STATES PATENT AND TRADEMARK OFFICE
CERTIFICATE OF CORRECTION

PATENT NO. : 7,383,732 B2  Page 1 of 1
APPLICATION NO. : 11/149176
DATED : June 10, 2008
INVENTOR(S) : Katsuya Okumura et al.

It is certified that error appears in the above-identified patent and that said Letters Patent is hereby corrected as shown below:

- On the title page, item (57), line 8, "a probe needles" should read --probe needles--;

Also, in the prior art there are two errors:

U.S: "2004/0066516 A1 issued 4/2004" should read --Deason et al--;

Foreign: "JP issued 2/1997" should read --09-033567--.

- In claim 2, column 24, line 26, "plurally" should read --plurality--;

- In claim 12, column 25, line 59, "outside:" should read --outside;--;

- In claim 18, column 26, line 52, "an micro structure" should read --a micro structure--;

- In claim 18, column 26, lines 60-61, "on then the" should read --on the--;

- In claim 21, column 27, line 15, "property" should read --properties--;

- In claim 22, column 27, line 29, "on then the" should read --on the--;

- In claim 25, column 28, lines 5-6, "said-micro structure" should read --said micro structure--;

Signed and Sealed this

Twenty-fourth Day of March, 2009

JOHN DOLL
*Acting Director of the United States Patent and Trademark Office*